United States Patent
Agarwal et al.

(10) Patent No.: US 10,828,171 B2
(45) Date of Patent: Nov. 10, 2020

(54) EXPANDABLE INTER-VERTEBRAL CAGE AND METHOD OF INSTALLING SAME

(71) Applicant: The University of Toledo, Toledo, OH (US)

(72) Inventors: Anand K. Agarwal, Toledo, OH (US); Vijay K. Goel, Toledo, OH (US); Aakash Agarwal, Toledo, OH (US); David Dick, Toledo, OH (US)

(73) Assignee: The University of Toledo, Toledo, OH (US)

( * ) Notice: Subject to any disclaimer, the term of this patent is extended or adjusted under 35 U.S.C. 154(b) by 283 days.

(21) Appl. No.: 14/904,224

(22) PCT Filed: Jul. 18, 2014

(86) PCT No.: PCT/US2014/047156
§ 371 (c)(1),
(2) Date: Jan. 11, 2016

(87) PCT Pub. No.: WO2015/009998
PCT Pub. Date: Jan. 22, 2015

(65) Prior Publication Data
US 2016/0143747 A1 May 26, 2016

Related U.S. Application Data

(60) Provisional application No. 61/847,841, filed on Jul. 18, 2013.

(51) Int. Cl.
*A61F 2/44* (2006.01)
*A61F 2/30* (2006.01)

(52) U.S. Cl.
CPC .. *A61F 2/4455* (2013.01); *A61F 2002/30092* (2013.01); *A61F 2002/30115* (2013.01);
(Continued)

(58) Field of Classification Search
CPC .......... A61F 2/44; A61F 2/4455; A61F 2/446; A61F 2/4465; A61F 2002/4415;
(Continued)

(56) References Cited

U.S. PATENT DOCUMENTS 5,383,694 A * 1/1995 Taeuber, Jr. .......... F16L 37/148
285/276
6,387,130 B1 * 5/2002 Stone .................... A61F 2/4455
623/17.16
(Continued)

FOREIGN PATENT DOCUMENTS

DE 10344019 B3 5/2005
WO 2013082184 A1 6/2013

OTHER PUBLICATIONS

PCT Written Opinion and International Search Report, Application No. PCT/US14/47156, dated Dec. 1, 2014.
(Continued)

*Primary Examiner* — Amy R Sipp
(74) *Attorney, Agent, or Firm* — MacMillan, Sobanski & Todd, LLC

(57) ABSTRACT

An intervertebral cage includes a plurality of segments that are connected together by one or more members formed from a shape memory alloy material such that the segments are automatically moved from an initial orientation before implantation/insertion in an intervertebral space to an expanded orientation after implantation/insertion in the intervertebral space. Each of the plurality of segments may have a plurality of passageways or recesses formed therethrough, and wherein a wire formed from a shape memory alloy material extends through each of the plurality of passageways or recesses. The member may be formed from
(Continued)

a shape memory alloy material that demonstrates shape memory effects and superelasticity properties, such as nitinol.

10 Claims, 16 Drawing Sheets

(52) U.S. Cl.
CPC ............ *A61F 2002/30462* (2013.01); *A61F 2002/30471* (2013.01); *A61F 2002/4415* (2013.01)

(58) Field of Classification Search
CPC ........ A61F 2002/4475; A61F 2002/448; A61F 2002/4485; A61F 2002/449; A61F 2002/30462; A61F 2002/30464; A61F 2002/30466; A61F 2002/30471
See application file for complete search history.

(56) References Cited

U.S. PATENT DOCUMENTS

| | | | | |
|---|---|---|---|---|
| 2001/0025542 | A1* | 10/2001 | Noetzold | F16C 1/26 74/502.5 |
| 2006/0142858 | A1 | 6/2006 | Colleran et al. | |
| 2006/0265077 | A1* | 11/2006 | Zwirkoski | A61F 2/4611 623/17.16 |
| 2008/0125865 | A1* | 5/2008 | Abdelgany | A61F 2/4425 623/17.16 |
| 2008/0221687 | A1* | 9/2008 | Viker | A61F 2/4611 623/17.16 |
| 2008/0243255 | A1* | 10/2008 | Butler | A61F 2/4465 623/17.16 |
| 2009/0030423 | A1* | 1/2009 | Puno | A61F 2/442 606/99 |
| 2009/0143859 | A1* | 6/2009 | McClellan, III | A61F 2/4455 623/17.16 |
| 2011/0009969 | A1* | 1/2011 | Puno | A61B 17/1757 623/17.12 |
| 2011/0046740 | A1 | 2/2011 | Chen et al. | |
| 2011/0245926 | A1 | 10/2011 | Kitchen | |
| 2012/0071980 | A1* | 3/2012 | Purcell | A61F 2/4455 623/17.16 |
| 2012/0083889 | A1 | 4/2012 | Purcell et al. | |
| 2013/0035762 | A1* | 2/2013 | Siegal | A61F 2/44 623/17.11 |
| 2013/0041471 | A1 | 2/2013 | Siegal et al. | |
| 2013/0144391 | A1* | 6/2013 | Siegal | A61F 2/442 623/17.16 |

OTHER PUBLICATIONS

The Extended European Search Report, Application No. 14826731.3 dated Mar. 30, 2017.

* cited by examiner

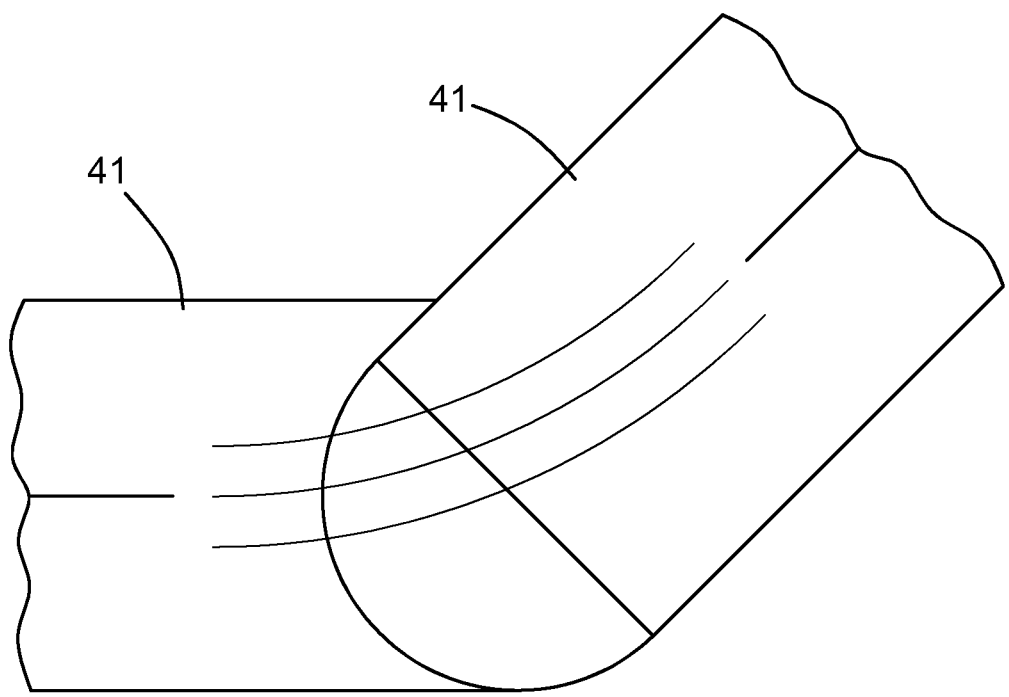
F I G. 25
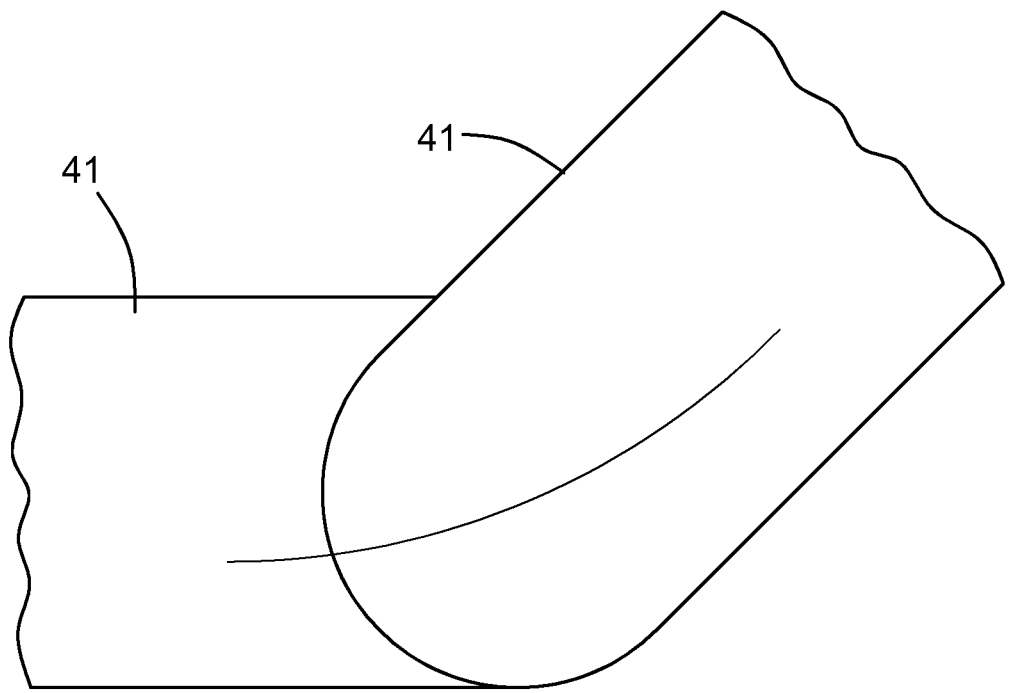
F I G. 26

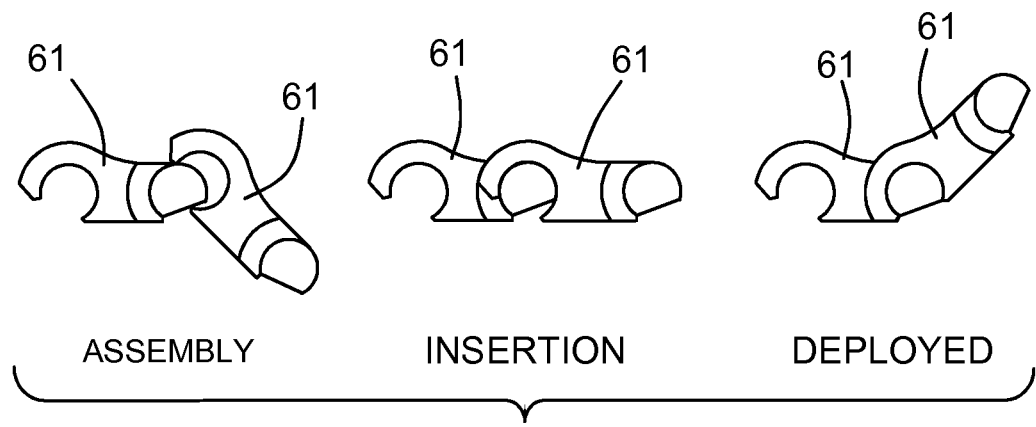
F I G. 31
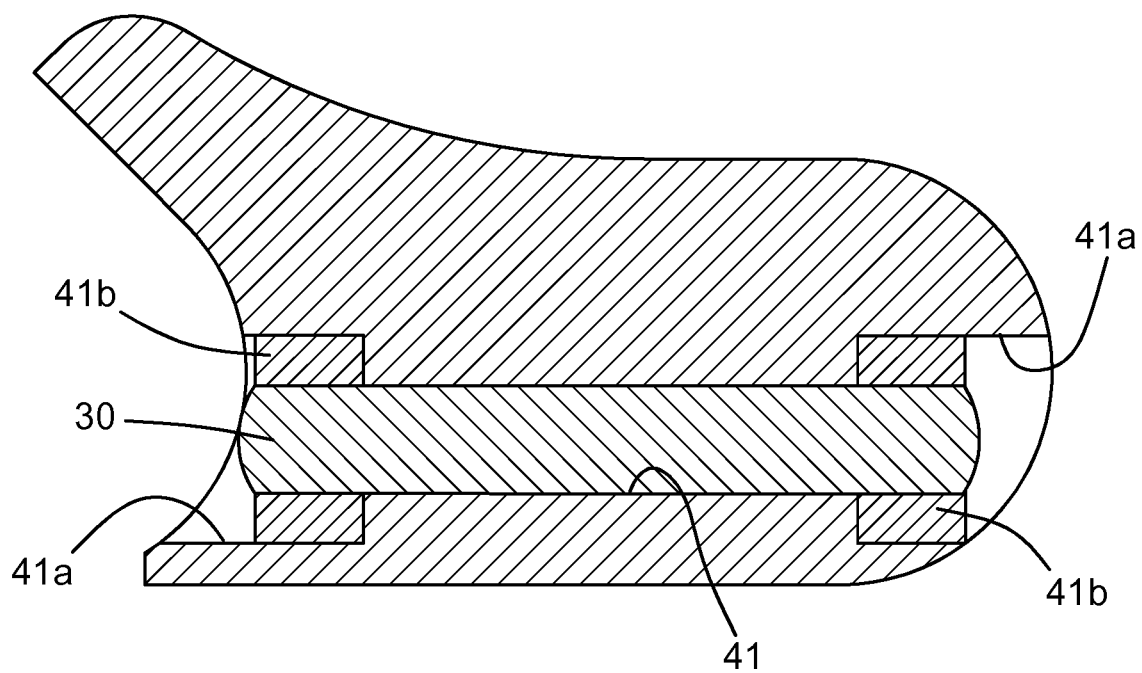
F I G. 32

EXPANDABLE INTER-VERTEBRAL CAGE AND METHOD OF INSTALLING SAME

STATEMENT REGARDING FEDERALLY SPONSORED RESEARCH

This invention was not made with any government support, and the government has no rights in this invention.

BACKGROUND OF THE INVENTION

This invention relates in general to the treatment of diseases of the spine using inter-vertebral devices and implantation methods. In particular, this invention relates to an automatically self-expanding inter-vertebral cage that can enter into a cavity through a small opening and automatically acquire any desired form as a result of either being released from an installation tool or being exposed to environmental conditions, such as temperature, moisture, light, magnetic field, electric field, pressure, etc. (or the lack thereof). More particularly, the self-expanding inter-vertebral cage of this invention can utilize shape memory alloy materials to accomplish the automatic activation.

Current expandable cages that utilize a standard hinge usually require a secondary activation force either during or after installation, such as by tightening a screw or by manually pushing walls of the cage from the center. This secondary activation force often necessitates more time and effort during the surgical procedure and, thus, increases the risk of complications and infection. Also, these cages generally require a larger incision than the proposed design because they are closed structures that define permanent cavities within the activation device. Other known cages have been designed utilizing shape memory alloy materials, but they similarly usually require a larger incision due to their "closed loop" design.

SUMMARY OF THE INVENTION

The inter-vertebral cage of this invention can include several interconnected cage sections that act as load bearing structures. Adjacent ones of the cage sections can be connected to one another by hinge elements formed from shape memory alloy materials, which can be in a torsionally stressed condition and such that they stay in place on their own. Alternatively, the hinge elements may be attached to the respective cage sections by a butt weld or other mechanism. The hinge elements may be bent so as to allow for more active wire within the hinge element such that a larger wire or tube may be used to provide higher restoring torque. The shape memory alloy material can withstand higher deformation than standard engineering metals and can also provide a constant force/torque over a wide range of linear/angular deformation. These properties will be utilized in creating a cage that will automatically activate into and hold a desired orientation during and after installation. The cage will be constructed in its desired shape with a small amount of pre-torque in the hinge element. Once assembled, the cage will assume the initial extended shape, causing the hinge elements to be torsionally stressed. The cage can then be placed within an installation device, such as an endoscope, which will hold the deformed shape until the cage is inserted within an inter-vertebral space. In doing this, the actuation of the shape memory/superelastic alloy will move an extended cage into a desired shape, preferably defining an open cavity for the placement of bone graft material. Following the placement of the graft material, a final securing screw can be applied to secure the end sections of the inter-vertebral cage and thereby close same. If additional rigidity is desired, the end sections of the inter-vertebral cage can be fixed together by means of one or more screws or other latching mechanism. Alternatively, the shape memory of the wire can be used to form hooks that would, when released from the insertion tool, contract to grab the end link to secure the end sections of the inter-vertebral cage and thereby close same.

Also, the cage sections may have pyramidal-shaped protrusions or other features provided on the top and/or bottom surfaces thereof to facilitate proper securing of the cage as a whole to the adjacent vertebral bodies. Thus, where a standard expandable cage would have all of the walls attached prior to insertion, the proposed design has an "open loop" design so that a much smaller horizontal profile is provided.

The installation of the inter-vertebral cage of this invention can be accomplished directly by means of a minimally invasive installation technique. Alternatively, a new technique is proposed for implanting this cage using an endoscope. The endoscope method is still minimally invasive in nature, but would allow direct visualization of every stage of the procedure by the surgeon, thereby reducing the number of potential complications. The configuration of the cage can be designed in such a way that it can be inserted by any known minimally invasive technique or by new techniques. The cage of this invention is advantageous over known cages in that it give optimal placement in the inter-vertebral space.

Various aspects of this invention will become apparent to those skilled in the art from the following detailed description of the preferred embodiments, when read in light of the accompanying drawings.

BRIEF DESCRIPTION OF THE DRAWINGS

FIG. 25 is a schematic drawing illustrating first dimensional relationships between the two segments of the third embodiment of the intervertebral cage shown in FIGS. 21 through 24.

FIG. 26 is a schematic drawing illustrating second dimensional relationships between the two segments of the third embodiment of the intervertebral cage shown in FIGS. 21 through 24.

FIG. 31 is a series of top plan views schematically illustrating how the segments of the intervertebral cage can be assembled, aligned for insertion, and oriented for deployment.

FIG. 32 is an enlarged sectional elevational view showing how a wire can be terminated in one of the segments of the intervertebral cage.

DETAILED DESCRIPTION OF THE PREFERRED EMBODIMENTS

Figure 1:
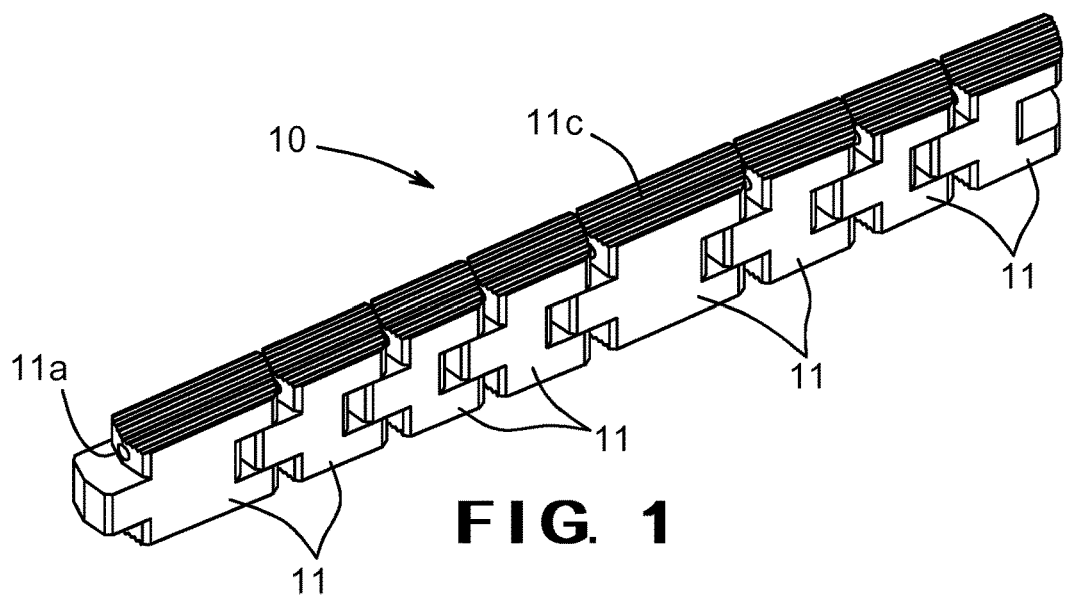
FIG. 1 is a perspective view of a first embodiment of an intervertebral cage in accordance with this invention shown in an initial orientation before implantation/insertion.
Figure 2:
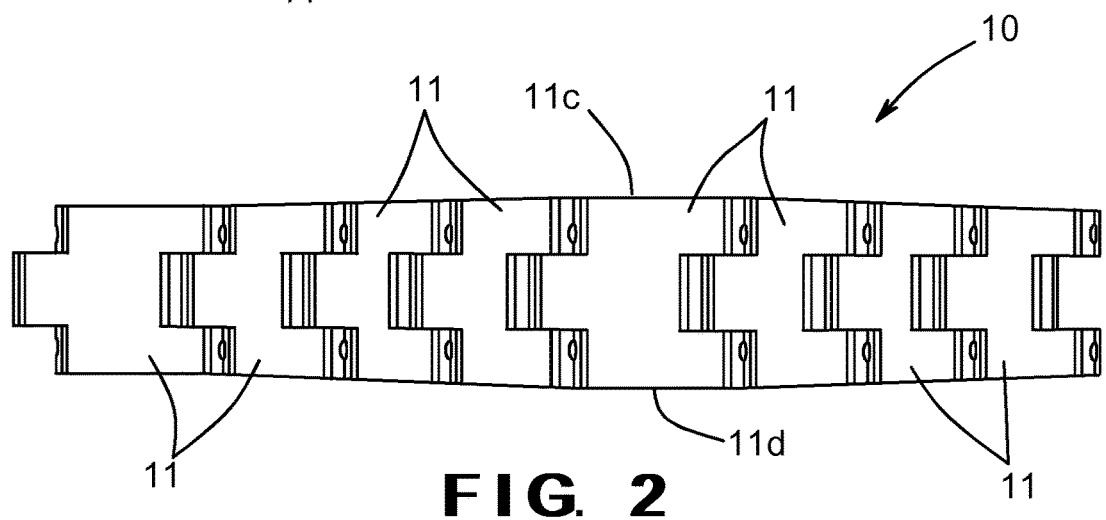
FIG. 2 is a side elevational view of the first embodiment of the intervertebral cage illustrated in FIG. 1.
Figure 3:
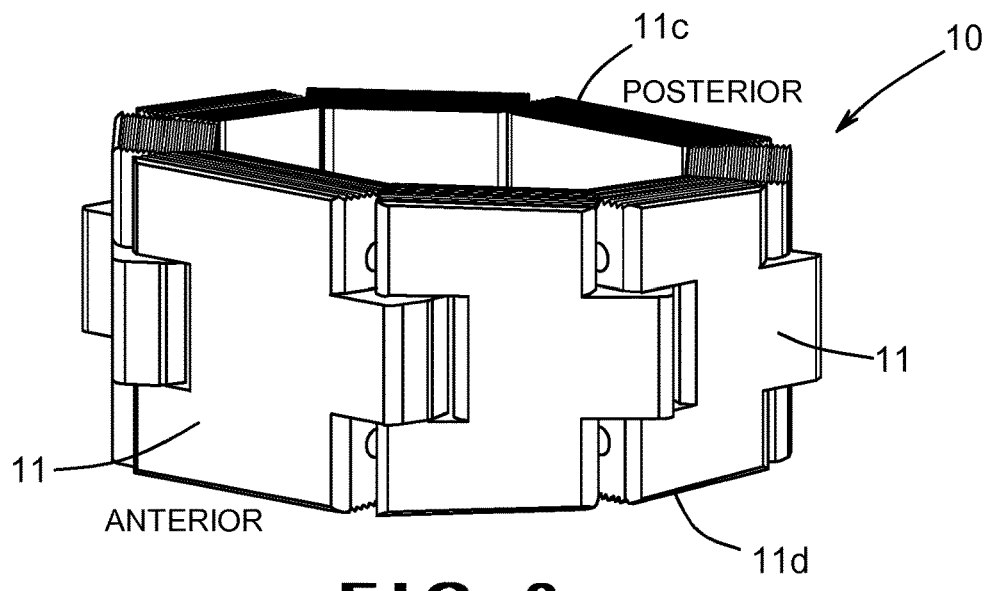
FIG. 3 is a perspective view of the first embodiment of the intervertebral cage illustrated in FIGS. 1 and 2 shown in an expanded orientation after implantation/insertion.
Figure 4:
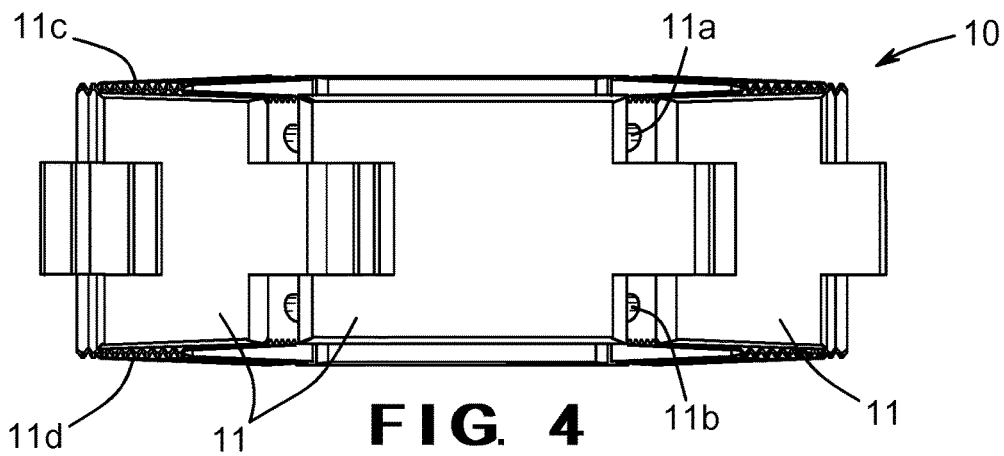
FIG. 4 is a first side elevational view of the first embodiment of the intervertebral cage illustrated in FIG. 3.

FIGS. 1 through 7 illustrate a first embodiment of the intervertebral cage, indicated generally at 10, in accordance with this invention. FIGS. 1 and 2 show the cage 10 in an initial orientation, which is the normal orientation of the cage 10 before implantation/insertion inside an intervertebral space, as discussed above. FIGS. 3 through 6 show the cage 10 is an expanded orientation, which is the normal orientation of the cage 10 after implantation/insertion inside an intervertebral space, as discussed above.

The illustrated cage 10 includes eight individual segments 11, although a greater or lesser number of same may be provided as desired. Each of the illustrated segments 11 has a first passageway 11a and a second passageway 11b formed therethrough, although such is not required. The first passageways 11a are preferably aligned with one another so that a first wire 30 (see FIG. 15) can extend through all of the segments 11. Similarly, the second passageways 11b are also preferably aligned with one another so that a second wire 30 can extend through all of the segments 11. Thus, the adjacent segments 11 are linked by two generally parallel wires 30 that pass through each of the segments 11. However, this invention contemplates that the cage 10 may be formed having either a greater or lesser number of such individual segments 11 and linking wires 30.

The segments 11 can have any desired height or combination of heights, such as, for example, from about 8 mm to about 18 mm. Similarly, the segments 11 can have any desired width or combination of widths, such as, for example, from about 3 mm to about 6 mm. The specific height(s) or width(s) of the segments 11 can vary in accordance with the size of the intervertebral space of the patient in which the cage 10 is to be implanted.

Figure 5:
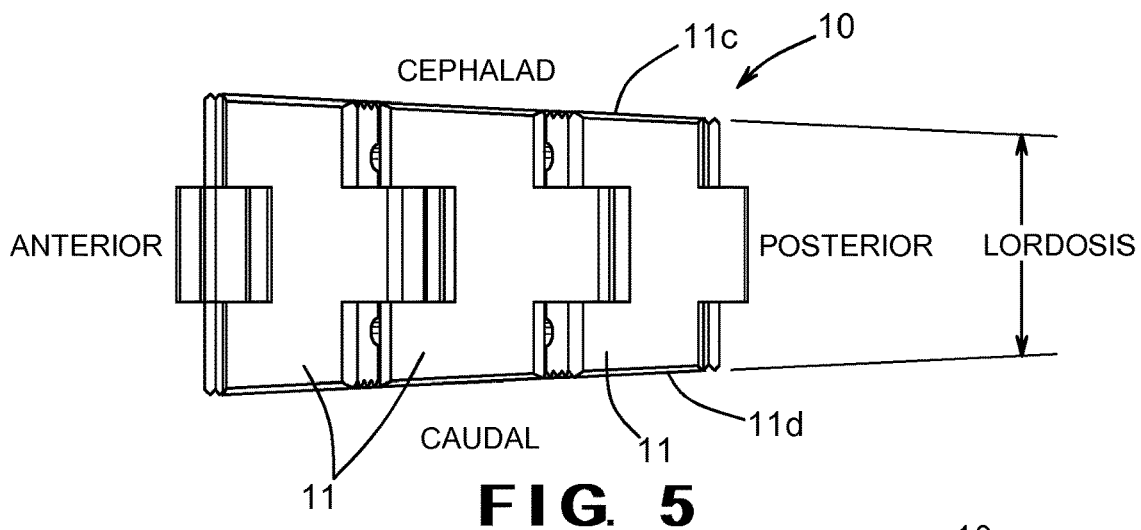
FIG. 5 is a second side elevational view of the first embodiment of the intervertebral cage illustrated in FIG. 3.
Figure 6:
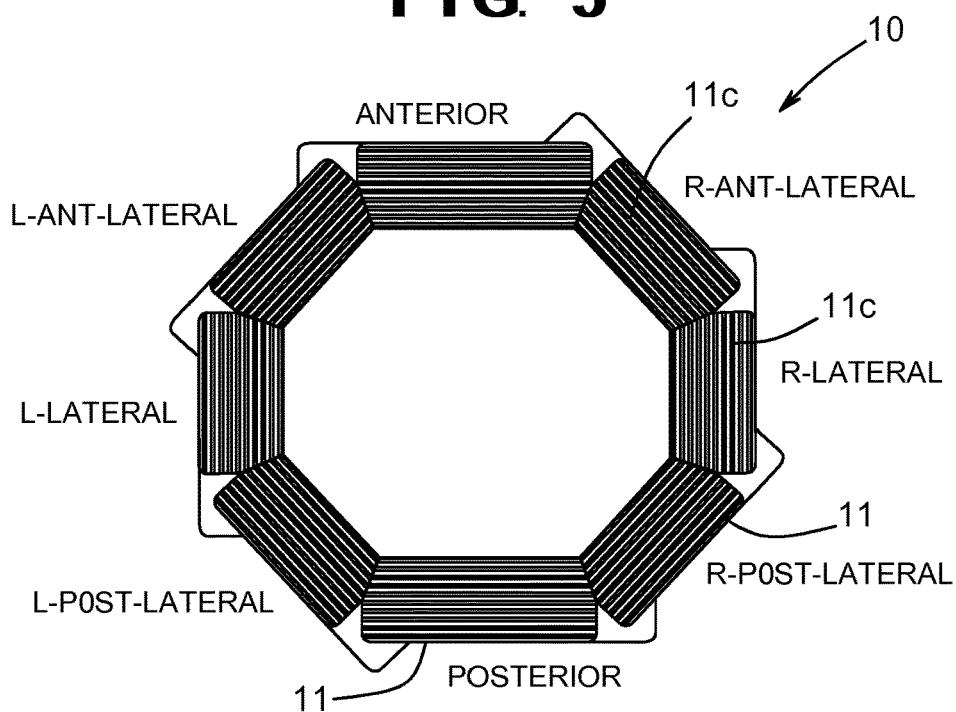
FIG. 6 is a top plan view of the first embodiment of the intervertebral cage illustrated in FIG. 3.

FIGS. 3, 4, 5, and 6 show the first embodiment of the intervertebral cage 10 an expanded orientation, which is the orientation that is obtained immediately after the cage 10 illustrated in FIGS. 1 and 2 is implanted or otherwise inserted inside the intervertebral space of the patient. As best shown in FIG. 5, the cage 10 can define a lordosis angle from an anterior portion of the cage 10 to a posterior portion thereof. The lordosis angle can be any desired value including, for example, in the range of from about 0 degrees to about 8 degrees depending upon the anatomy and other needs of the patient.

Figure 7:
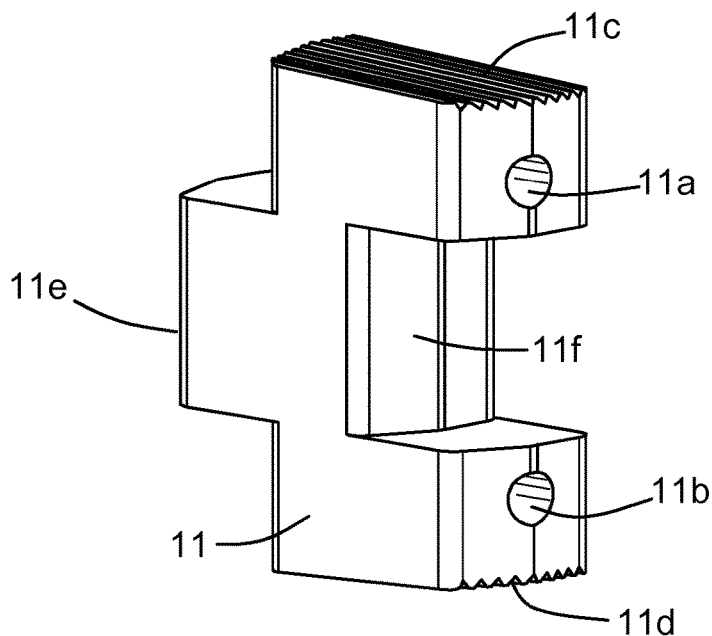
FIG. 7 is an enlarged perspective view of one of the segments of the intervertebral cage illustrated in FIGS. 1 through 6.

FIG. 7 shows a single one of the plurality of the segments 11 (anterior, in this case) of the first preferred embodiment of the intervertebral cage 10. The illustrated segment 11 includes the two passageways 11a and 11b that, as discussed above, are provided for the two wires 30 to pass therethrough. The illustrated segment 11 also includes serrations 11c and 11d on the cephalad and caudal faces that are provided for rough contact with the endplates of the adjacent vertebrae of the spine of the patient after implantation. Also, the segment 11 includes a central offset region that defines an extension portion 11e and a recessed portion 11f. As shown in FIGS. 1 through 6, the extension portions 11e of the segments 11 are received within the recessed portions 11f of the adjacent segments 11 when the intervertebral cage 10 is assembled.

The segments 11 of the intervertebral cage 10 can be formed from any desired material. For example, some or all of the segments 11 may be formed from one or more metallic materials (such as titanium, for example), one or more polymeric materials (such as PEEK and PEAK, for example), or one or more composite materials (such as ENDOLIGN® brand implantable polymer composite, for example). These biomaterials are preferably of medical grade whose efficacy has been shown in clinical studies.

Figure 8:
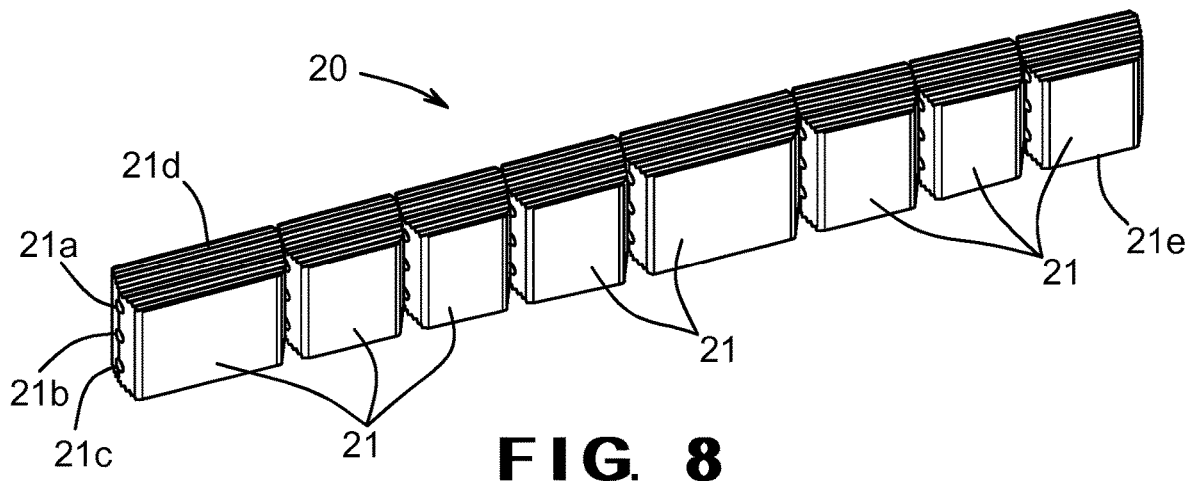
FIG. 8 is a perspective view of a second embodiment of an intervertebral cage in accordance with this invention shown in an initial orientation before implantation/insertion.
Figure 9:
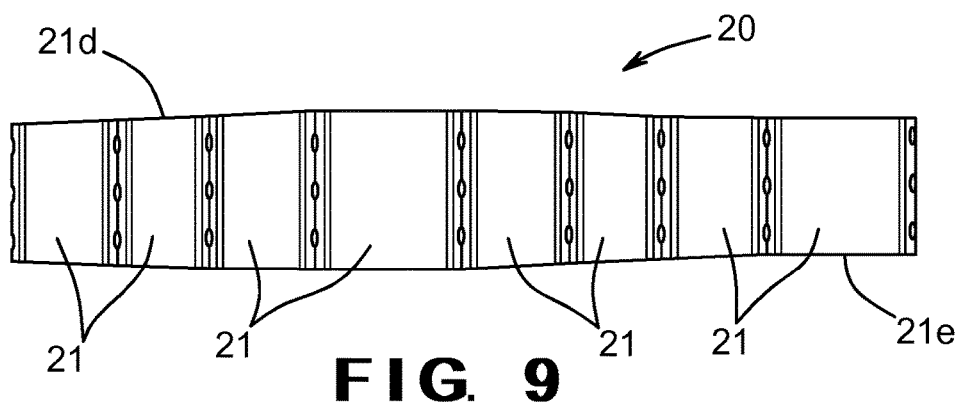
FIG. 9 is a side elevational view of the second embodiment of the intervertebral cage illustrated in FIG. 8.
Figure 10:
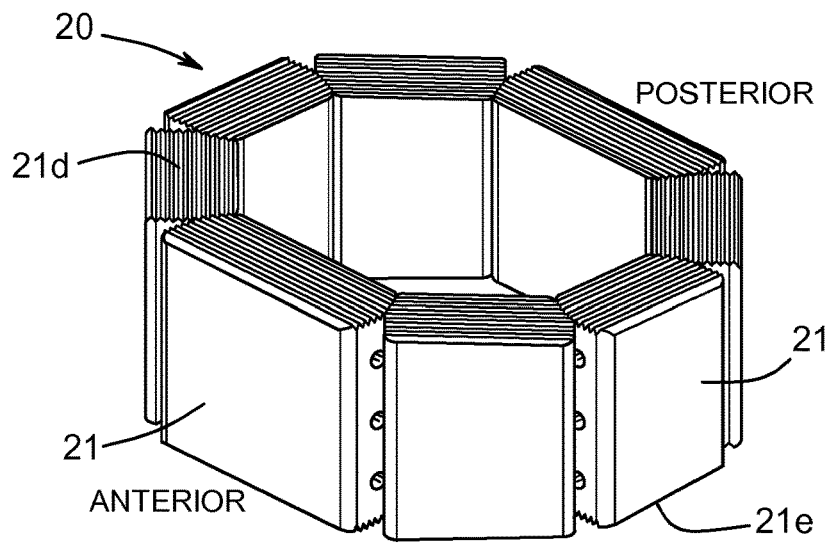
FIG. 10 is a perspective view of the second embodiment of the intervertebral cage illustrated in FIGS. 8 and 9 shown in an expanded orientation after implantation/insertion.
Figure 11:
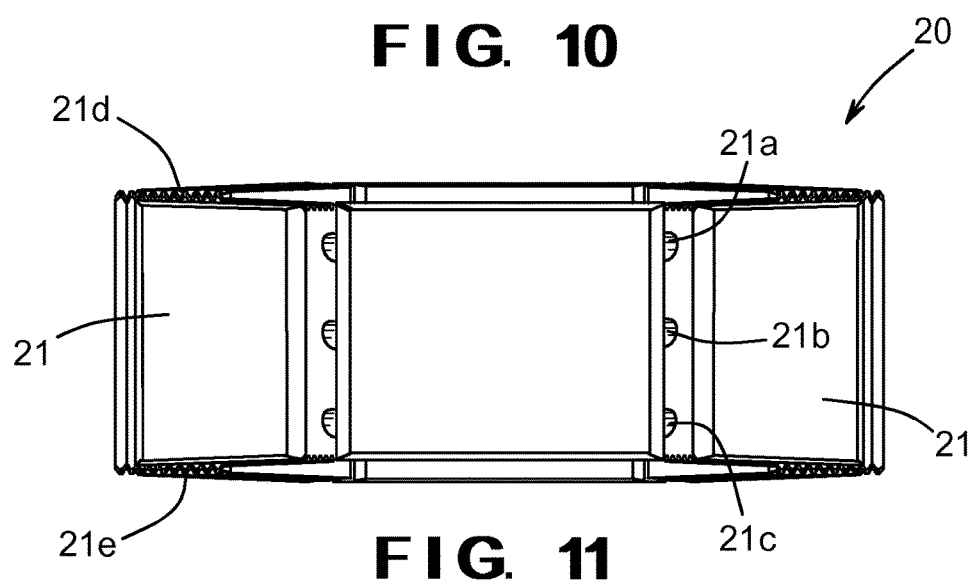
FIG. 11 is a first side elevational view of the second embodiment of the intervertebral cage illustrated in FIG. 10.

FIGS. 8 through 14 illustrate a second embodiment of the intervertebral cage, indicated generally at 20, in accordance with this invention. FIGS. 8 and 9 show the cage 20 in an initial orientation, which is the normal orientation of the cage 20 before implantation/insertion inside an intervertebral space, as discussed above. FIGS. 10 through 13 show the cage 20 is an expanded orientation, which is the normal orientation of the cage 20 after implantation/insertion inside an intervertebral space, as discussed above.

The illustrated cage 20 includes eight individual segments 21, although a greater or lesser number of same may be provided as desired. Each of the illustrated segments 21 has a first passageway 21a, a second passageway 21b, and a third passageway 21c formed therethrough, although such is not required. The first passageways 21a are preferably aligned with one another so that a first wire 30 can extend through all of the segments 21. Similarly, the second and third passageways 21b and 21c are also preferably aligned with one another so that second and third wires 30 can respectively extend through all of the segments 21. Thus, the adjacent segments 21 are linked by three generally parallel wires 30 that pass through each of the segments 21. However, this invention contemplates that the cage 20 may be formed having either a greater or lesser number of such individual segments 21 and linking wires 30.

The segments 21 can have any desired height or combination of heights, such as, for example, from about 8 mm to about 18 mm. Similarly, the segments 21 can have any desired width or combination of widths, such as, for example, from about 3 mm to about 6 mm. The specific height(s) or width(s) of the segments 21 can vary in accordance with the size of the intervertebral space of the patient in which the cage 20 is to be implanted.

Figure 12:
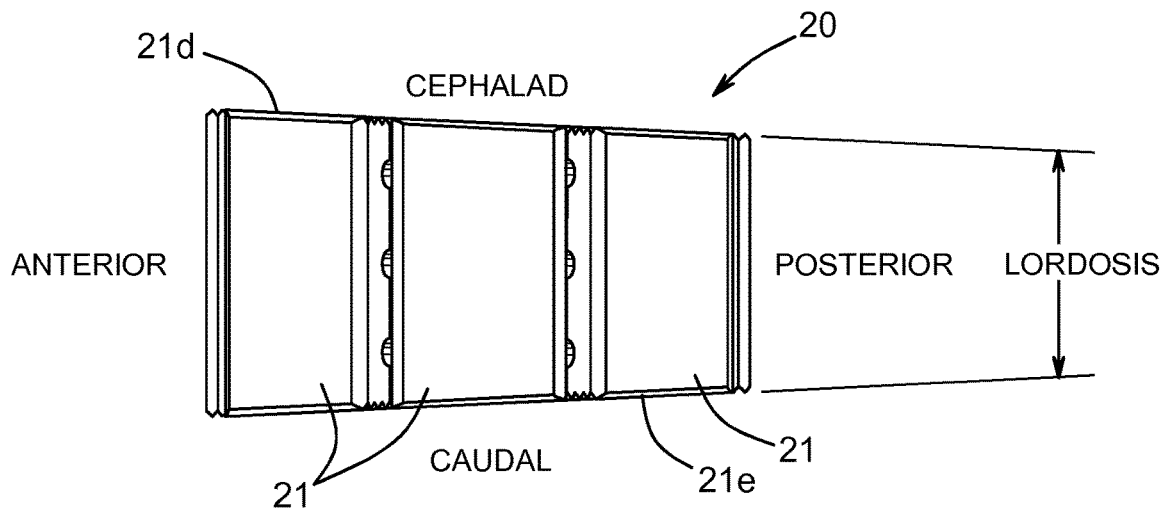
FIG. 12 is a second side elevational view of the second embodiment of the intervertebral cage illustrated in FIG. 10.
Figure 13:
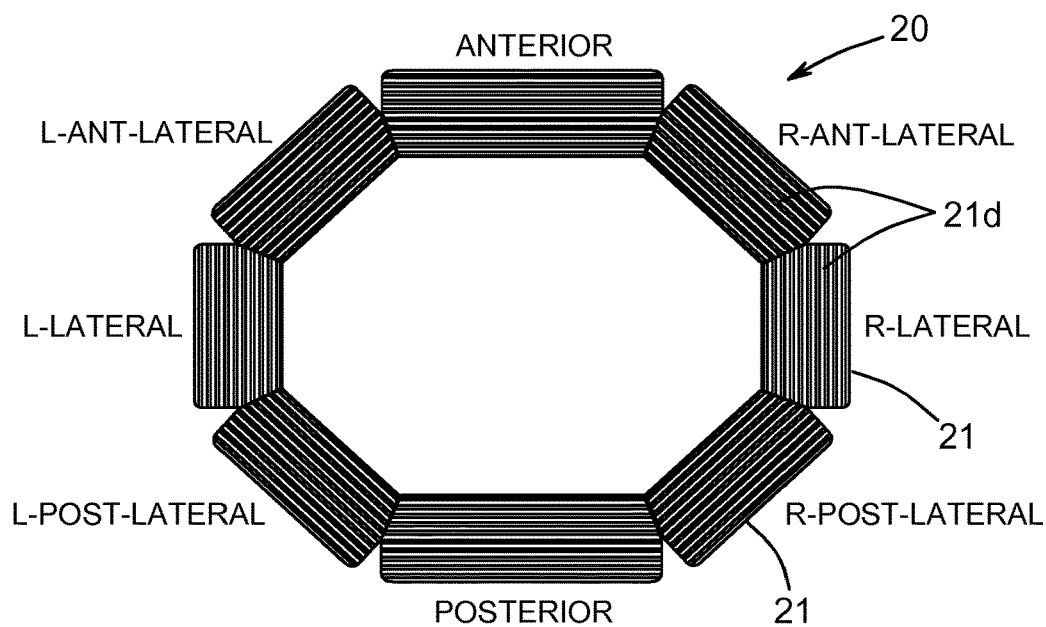
FIG. 13 is a top plan view of the second embodiment of the intervertebral cage illustrated in FIG. 10.

FIGS. 10, 11, 12, and 13 show the second embodiment of the intervertebral cage 20 in an expanded orientation, which is the orientation that is obtained immediately after the cage 20 illustrated in FIGS. 8 and 9 is implanted or otherwise inserted inside the intervertebral space of the patient. As best shown in FIG. 12, the cage 10 can define a lordosis angle from an anterior portion of the cage 20 to a posterior portion thereof. The lordosis angle can be any desired value including, for example, in the range of from about 0 degrees to about 8 degrees depending upon the anatomy and other needs of the patient.

Figure 14:
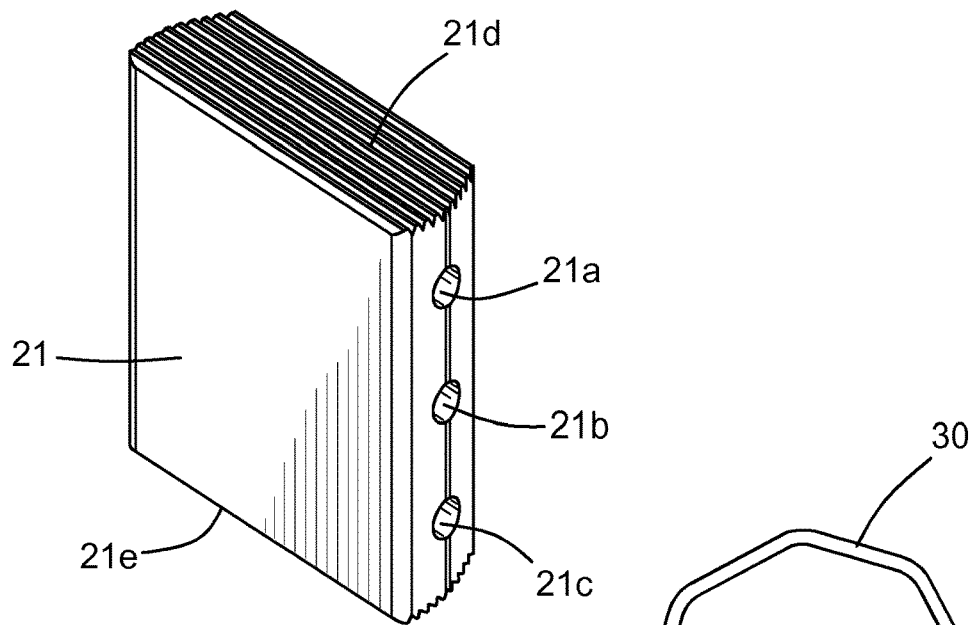
FIG. 14 is an enlarged perspective view of one of the segments of the intervertebral cage illustrated in FIGS. 8 through 13.

FIG. 14 shows a single segment 21 (anterior, in this case) of the first preferred embodiment of the intervertebral cage 20. The illustrated segment 21 includes the three passageways 21a, 21b, and 21c that, as discussed above, are provided for the three wires 30 to pass therethrough. The illustrated segment 21 also includes serrations 21d and 21e on the cephalad and caudal faces that are provided for rough contact with the endplates of the adjacent vertebrae of the spine of the patient after implantation.

The segments 21 of the intervertebral cage 20 can be formed from any desired material. For example, some or all of the segments 21 may be formed from one or more metallic materials (such as titanium, for example), one or more polymeric materials (such as PEEK and PEAK, for example), or one or more composite materials (such as ENDOLIGN® brand implantable polymer composite, for example). These biomaterials are preferably of medical grade whose efficacy has been shown in clinical studies.

Figure 15:
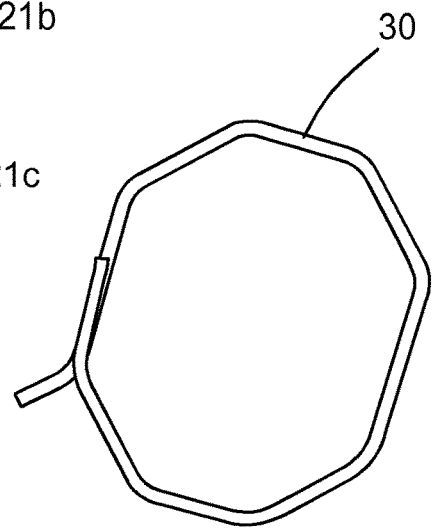
FIG. 15 is a top plan view of a superelastic/shape memory wire shown in a non-stressed form.

FIG. 15 illustrates one of the wires 30 that can be used in the intervertebral cages 10 and 20 described above. In the illustrated embodiment, the wire 30 is generally octagonal in its non-stressed form, which corresponds with its use in the cages 10 and 20 having eight segments 11 and 21, respectively. However, the wires 30 may have any desired shape or combination of shapes. The wire 30 is preferably formed from a shape memory alloy material that demonstrates shape memory effects and superelasticity properties. For example, during the shape memory effect, the material, at low temperature, may transform from a twinned martensite phase to de-twinned (deformed) martensite phase. Thereafter, upon heating above the transition temperature, the material will transform from de-twinned martensite phase to an austenite phase. During the superelastic effect, the material, at high temperature, will deform extensively by transforming from the austenite phase to the martensite phase upon continual application of force. It will, however, immediately recover to un-deformed shape (and the austenite phase) upon removal of applied force. One example of a preferred material for use as the shape memory alloy wire is nitinol. However, other shape memory or superelastic materials could also be used as well.

Figure 16:
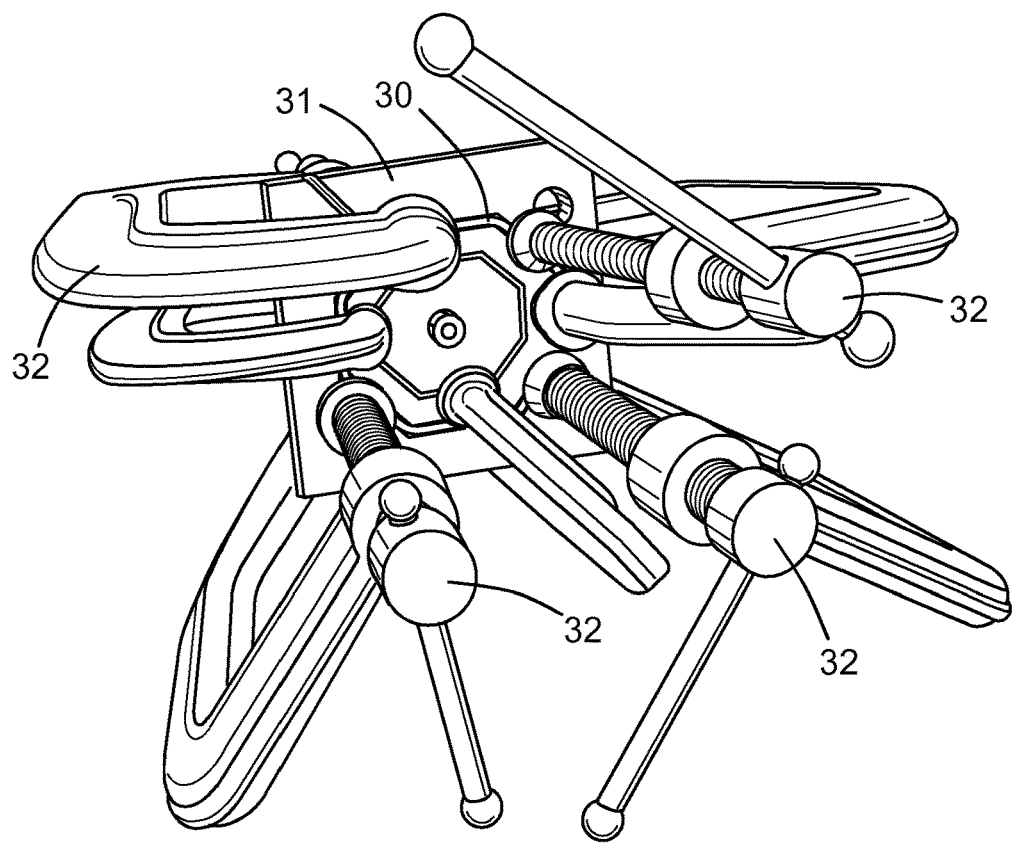
FIG. 16 is a perspective view of the superelastic/shape memory wire illustrated in FIG. 15 shown inside a mandrel and forced into a desired shape by a plurality of clamps.
Figure 17:
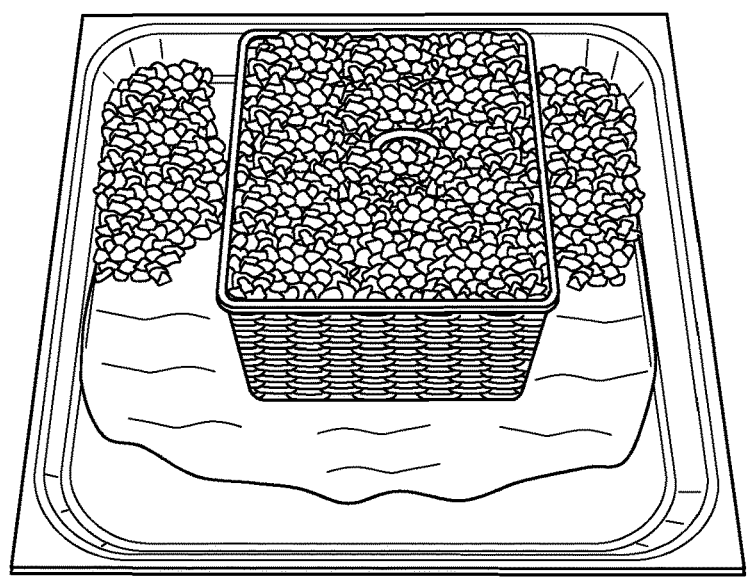
FIG. 17 is a perspective view of an ice bath for rapidly cooling the superelastic/shape memory wire after removal from an oven.
Figure 18:
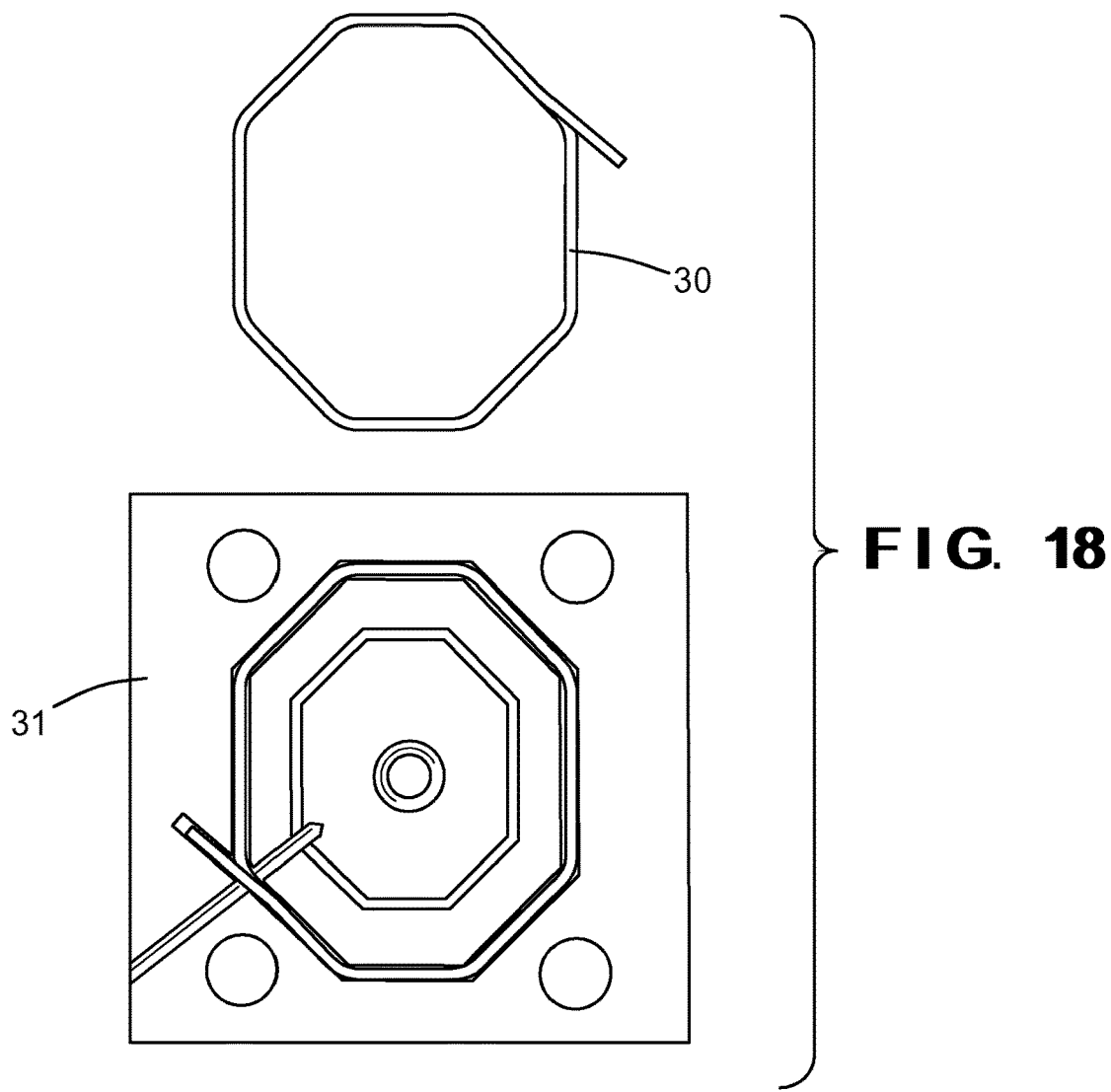
FIG. 18 is a top plan view showing the superelastic/shape memory wire after heat treatment and rapid cooling and a mandrel for manufacturing same.
Figure 19:
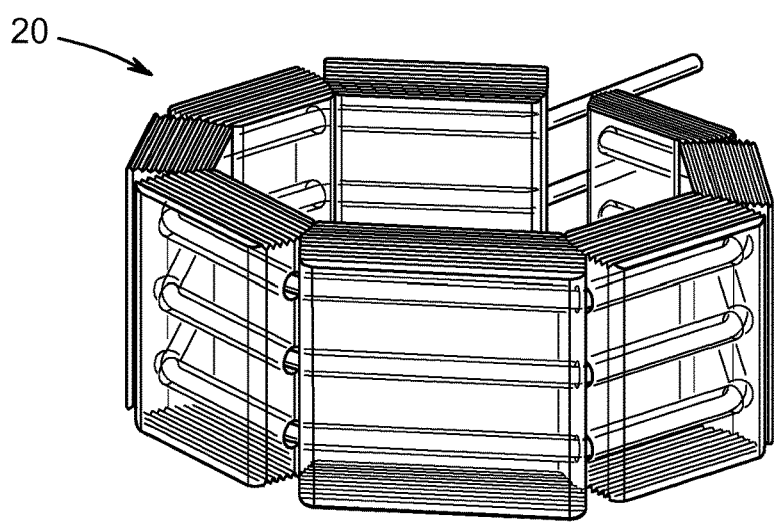
FIG. 19 is an anterior perspective view of the second embodiment of the assembled cage.
Figure 20:
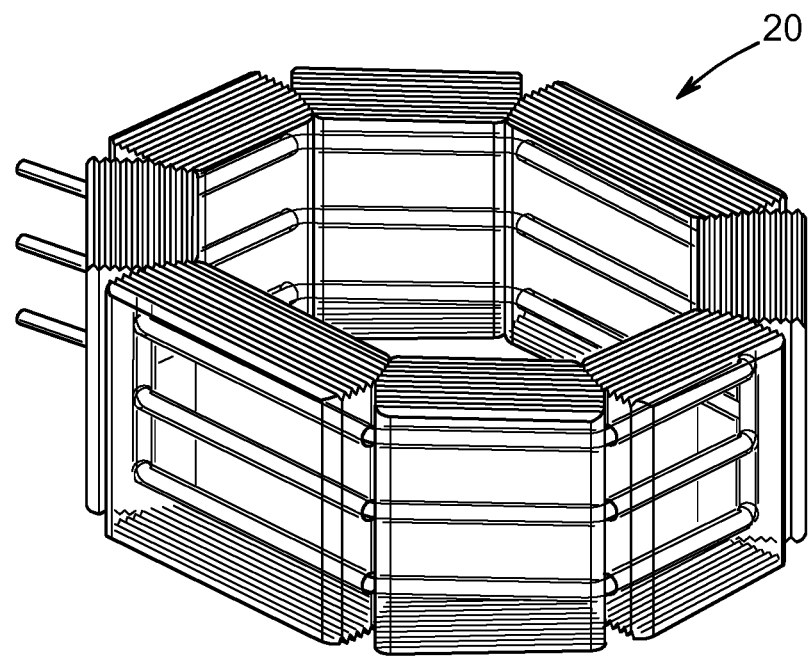
FIG. 20 is a lateral perspective view of the second embodiment of the assembled cage.
Figure 21:
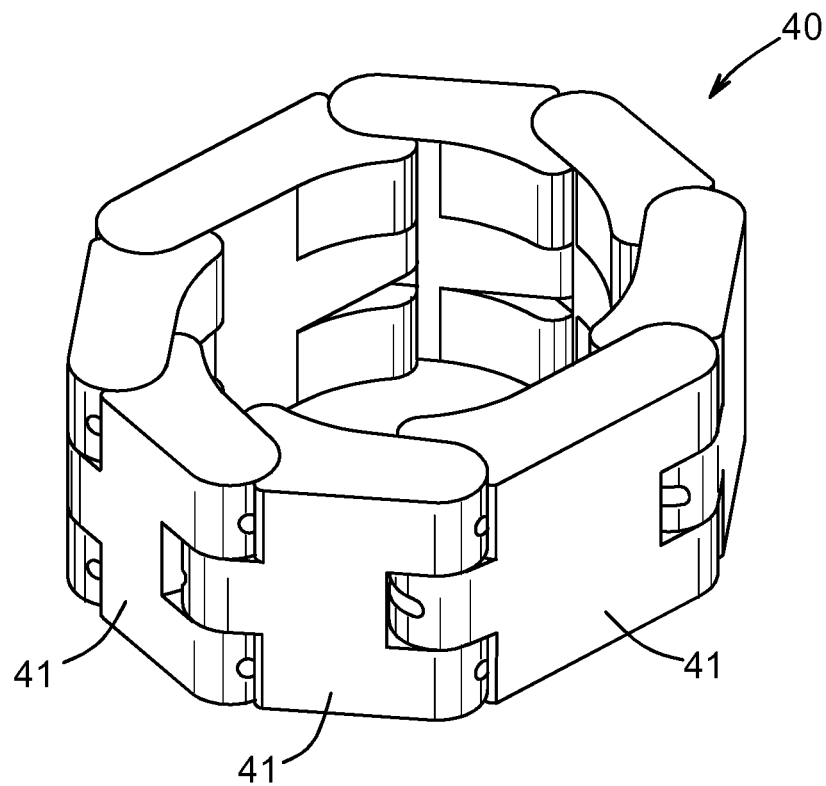
FIG. 21 is a perspective view of a third embodiment of the intervertebral cage shown in an expanded orientation after implantation/insertion.

The wire 30 can be initially obtained having a straight shape, then processed as shown in FIGS. 16, 17, and 18 to form the octagonal or other desired shape. As shown in FIG. 16, the wire 30 can be initially disposed inside an octagonal recess provided in a mandrel 31. A force is applied though one or more clamps 32 to hold the wire in the octagonal recess. Due to this applied force, the austenite phase of the wire 30 will transform into martensite phase. The wire 30 is above its transition temperature. The system is then heated up to 500 degrees Celsius and thereafter rapidly cooled in an ice bath, as shown in FIG. 17. This heat treatment, followed by rapid cooling, sets the wire 30 in the desired octagonal shape, as shown in FIG. 18. The wires 30 are then put through each segment 11 and 21 of the cage 10 and 20 to provide the cage assembly. FIGS. 19 and 20 illustrate the anterior and side views of the assembled cage 20 of the second preferred embodiment.

Figure 22:
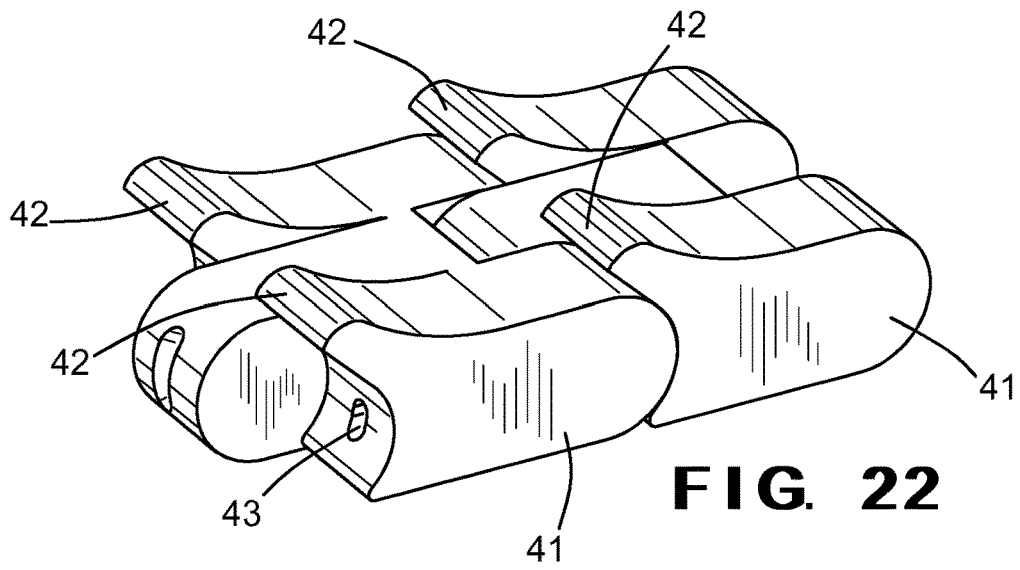
FIGS. 22 and 23 are enlarged perspective views of two of the segments of the third embodiment of the intervertebral cage shown in FIG. 21 shown in a linear orientation.
Figure 23:
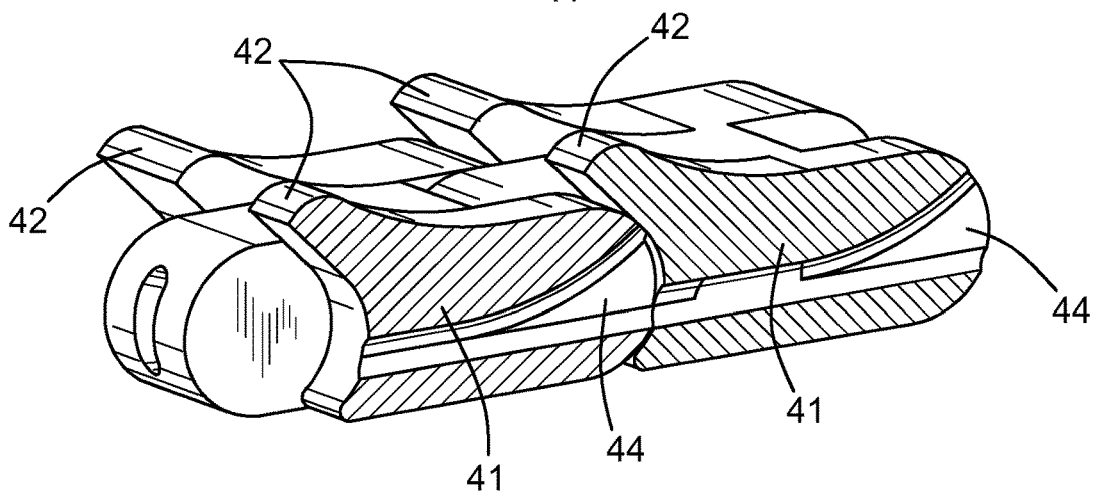
Figure 24:
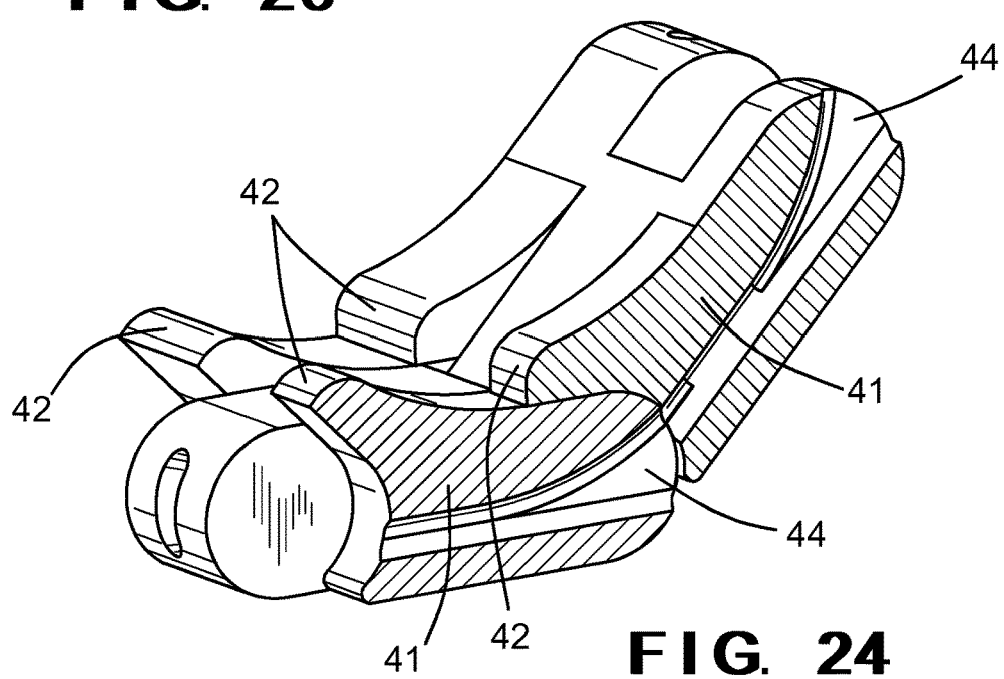
FIG. 24 is an enlarged perspective view of two of the segments of the third embodiment of the intervertebral cage shown in FIG. 21 shown in an angled orientation.

FIGS. 21 through 26 illustrate a third embodiment of an intervertebral cage, indicated generally at 40, in accordance with this invention. The illustrated cage 40 includes eight individual segments 41, although a greater or lesser number of same may be provided as desired. Each of the illustrated segments 41 includes one or more passageways and wires so that the adjacent segments 41 are linked by the wires as described above. In this embodiment, however, the mating surfaces of the adjacent segments 41 have interlocking protrusions 42 provided thereon. Mating surfaces may be provided on adjacent segments 41 that are generally cylindrical in shape to facilitate articulation of the adjacent segments 41. The protrusions 42 serve to both (1) limit the amount of articulation of the adjacent segments 41 and thereby control the deployed device shape, and (2) provide a guide groove along the length of the cage 40 in the generally linear insertion configuration. As shown in FIG. 22, the adjacent segments 41 may be provided with one or more internal passageways 43 (only one is illustrated) to accommodate reinforcing wires 30 in the manner described above. Alternatively, as shown in FIGS. 23 and 24, the adjacent segments 41 may be provided with external recesses 44 to accommodate reinforcing wires. The internal passageways 43 and the external recesses 44 may be extended at either or both ends to allow passage of the wires 30 in both the insertion and deployed orientations of the cage 40. The outer extents of the internal passageways 43 and the external recesses 44 may be straight to serve in the insertion state, while the inner extents of the internal passageways 43 and the external recesses 44 may be curved to match the design wire bend radius in the insertion state. This bend radius may be chosen to maintain the wire bend radius within an elastic range so the properties of the nitinol shape memory feature can be used for pre-shaping the wires 30. The wires 30 can be terminated in the end links, such as by welding the wire ends to suitable nitinol washers or sleeves countersunk into the links.

FIG. 25 shows the geometry of a joint between adjacent segments 41. As shown therein, a wire channel is centered in the segments 41 and passes through the segment pivot point. The length of the curve is less than the length of the straight sections over the same link geometry, such as 0.33 mm for each joint, for example. If the wire was installed tight in the straight insertion configuration, after deployment it may have over 2.5 mm of excess length. However, if the wire channel is moved outward from the centerline the straight section distance drops. FIG. 26 shows an offset of about 0.75 mm, and the arc length is shorter than the straight line length. In this case, the wire would be 2.3 mm too short after deployment. The lengths match at around 0.6 mm of offset. This could be useful in that it allows an offset to be selected that would provide any desired amount of compression to the cage, keeping the joints tight and helping with fatigue strength. The wires provide compression, so having more material toward the inside of the curve is advantageous.

Figure 27:
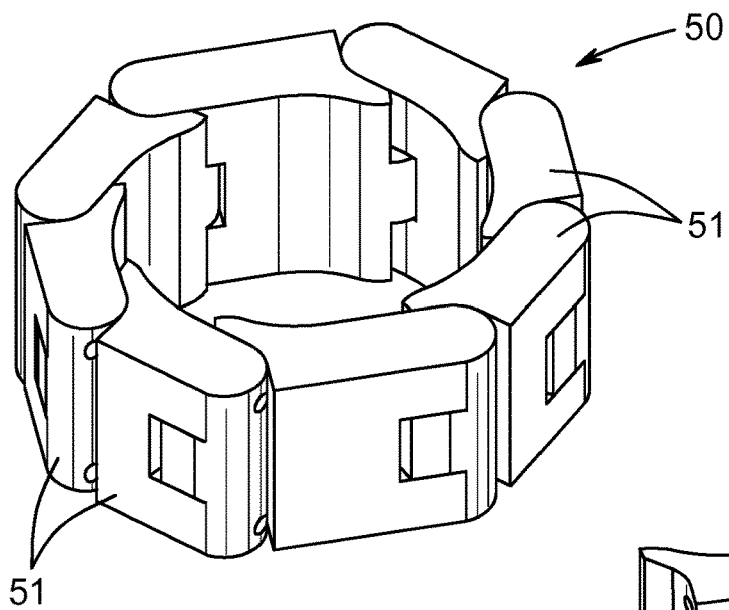
FIG. 27 is a perspective view of a fourth embodiment of the intervertebral cage shown in an expanded orientation after implantation/insertion.
Figure 28:
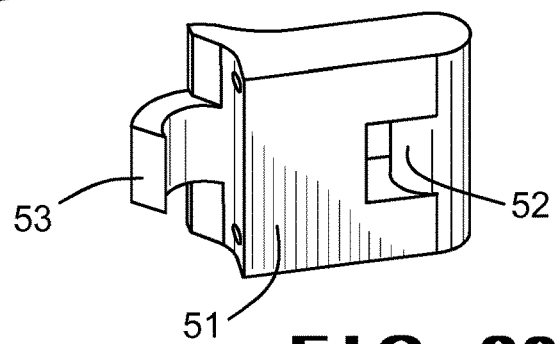
FIG. 28 is an enlarged perspective view of one of the segments of the fourth embodiment of the intervertebral cage shown in FIG. 27.

FIGS. 27 and 28 illustrate a fourth embodiment of an intervertebral cage, indicated generally at 50, that is formed from a plurality segments 51 in accordance with this invention. In this embodiment, each of the segments 51 includes a pivot support surface 52 provided at a first end and a pivot arm 53 provided at a second end. As best shown in FIG. 27, the segments 51 can be assembled by causing the pivot arm 53 of each segment 53 to engage the pivot support surface 52 of an adjacent segment 51.

Figure 29:
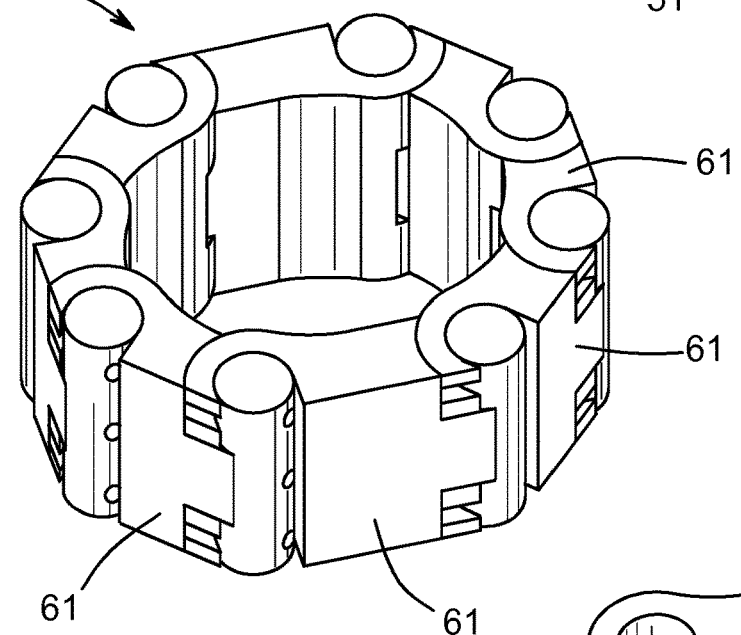
FIG. 29 is a perspective view of a fifth embodiment of the intervertebral cage shown in an expanded orientation after implantation/insertion.
Figure 30:
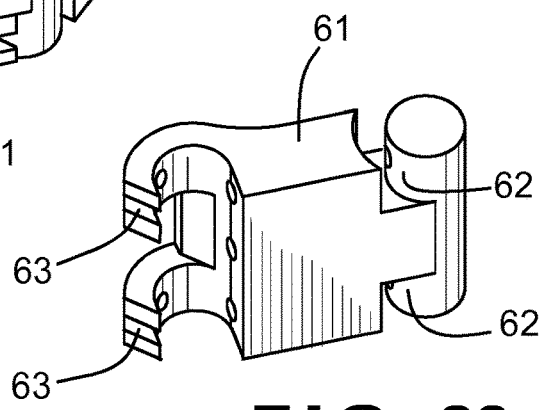
FIG. 30 is an enlarged perspective view of one of the segments of the fifth embodiment of the intervertebral cage shown in FIG. 29.

FIGS. 29 and 30 illustrate a fifth embodiment of an intervertebral cage, indicated generally at 60, that is formed from a plurality segments 61 in accordance with this invention. In this embodiment, each of the segments 61 includes a pair of pivot support surfaces 62 provided at a first end and a pair of pivot arms 63 provided at a second end. As best shown in FIG. 29, the segments 61 can be assembled by causing the pivot arms 63 of each segment 63 to engage the pivot support surfaces 62 of an adjacent segment 61.

FIG. 31 is a series of top plan views schematically illustrating how the segments of the intervertebral cages 50 and 60 can be assembled, aligned for insertion, and oriented for deployment.

FIG. 32 is an enlarged sectional elevational view showing how a wire 30 can be terminated in one of the segments, such as one of the segments 41 of the intervertebral cage 40, for example. The wire 30 may be terminated in either or both of the first and last segments 41 of the cage 40. FIG. 32 shows the wire 30 having both ends terminated in a single segment 40 for simplicity. As shown therein, the terminal ends of the segment 40 are each provided with a cylindrical recess 41a. A sleeve 41b is passed over the end of the wire 30, and the sleeves 41b and the wire 30 are joined by welding. Alternatively, one end of the wire 30 could have an enlarged stop formed therein that engages the head of the sleeve 41b, while the other end of the wire 30 can be terminated in the manner described above. Also, the sleeves 41b could be replaced with bars (not shown) that extend laterally across all or some portion of the nose or tail of the segment 40. The bars would be contoured to match the outer contour of the segment 40. These bars would be provided with holes for the one, two, or three (or more) of the wires 30 used to secure the segments 40 together. Each wire 30 could be welded to the bar or bars.

Figure 33:
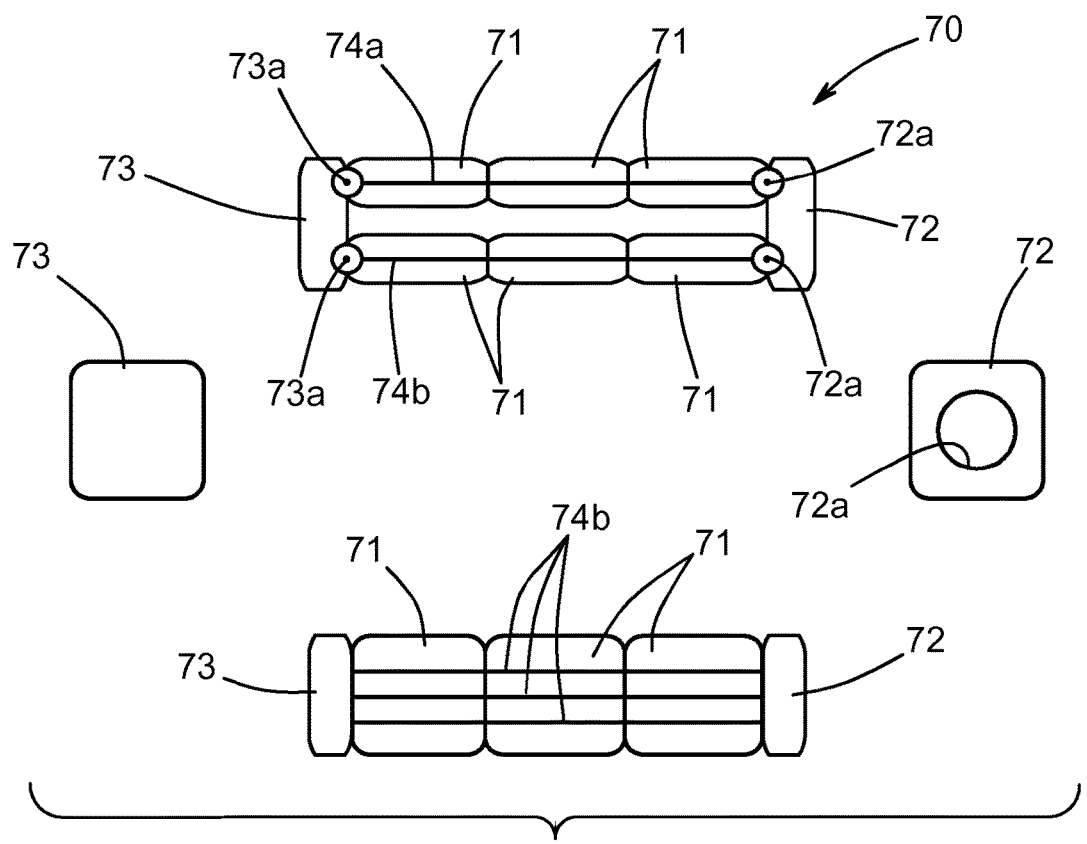
FIG. 33 is a series of views showing a sixth embodiment of an intervertebral cage in accordance with this invention.
Figure 34:
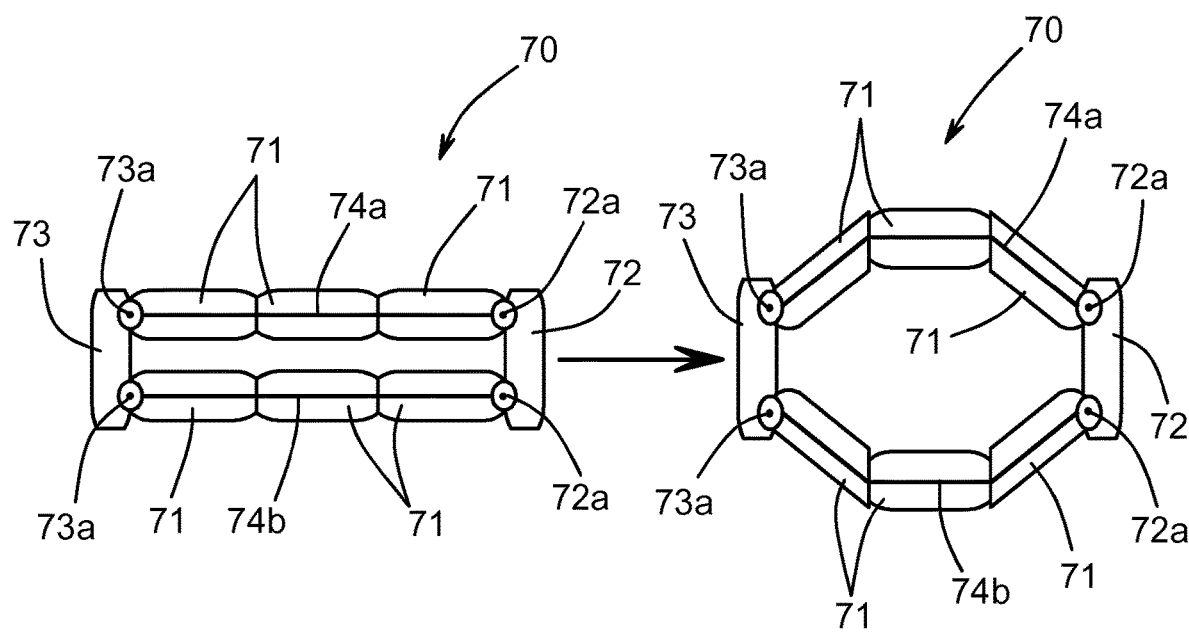
FIG. 34 is a pair of views showing the sixth embodiment of the intervertebral cage in both an initial contracted shape and a final implanted shape.

FIGS. 33 and 34 illustrate a sixth embodiment of an intervertebral cage, indicated generally at 70, in accordance with this invention. The sixth embodiment of the intervertebral cage 70 includes a plurality of side segments 71 and a plurality of end segments 72 and 73. In the illustrated embodiment, the intervertebral cage 70 includes six side segments 71 and two end segments 72 and 73, although a greater or lesser number of each may be provided. The end segment 72 is provided with a pair of hinges 72a, and the end segment 73 is provided with a similar pair of hinges 73a. A first wire or first plurality of wires 74a extends through a first group of the side segments 71 from a first one of the hinges 72a provided on the first end segment 72 to a first one of the hinges 73a provided on the second end segment 73. Similarly, a second wire or second plurality of wires 74b extends through a second group of the side segments 71 from a second one of the hinges 72a provided on the first end segment 72 to a second one of the hinges 73a provided on the second end segment 73. In the illustrated embodiment, three of each of the wires 74a and 74b are utilized, although a greater or lesser number may be provided. The illustrated wires 74a and 74b extend generally parallel to one another, although again such is not required. The illustrated end segment 72 is provided with a hole 72a that allows the insertion of a bone graft material therethrough. To accomplish this, the hole may have a threaded inner surface (not shown) that can cooperate with a complementary threaded outer surface provided on a cannulated device (not shown). The hole 72a can also be used for insertion of balloon or other mechanical device to help in expansion of intervertebral cage 70 if desired, as described below in connection with FIGS. 37 and 38. The wires 74a and 74b may be formed from a shape memory material, such as nitinol, that allows the intervertebral cage 70 to expand to the expanded shape, revert back to the initial contracted shape, or otherwise automatically acquire any other desired shape. However, the hinges 72a and 73a may allow for unconstrained rotation between the end segments 72 and 73 and the side segments 71 connected thereto.

Figure 35:
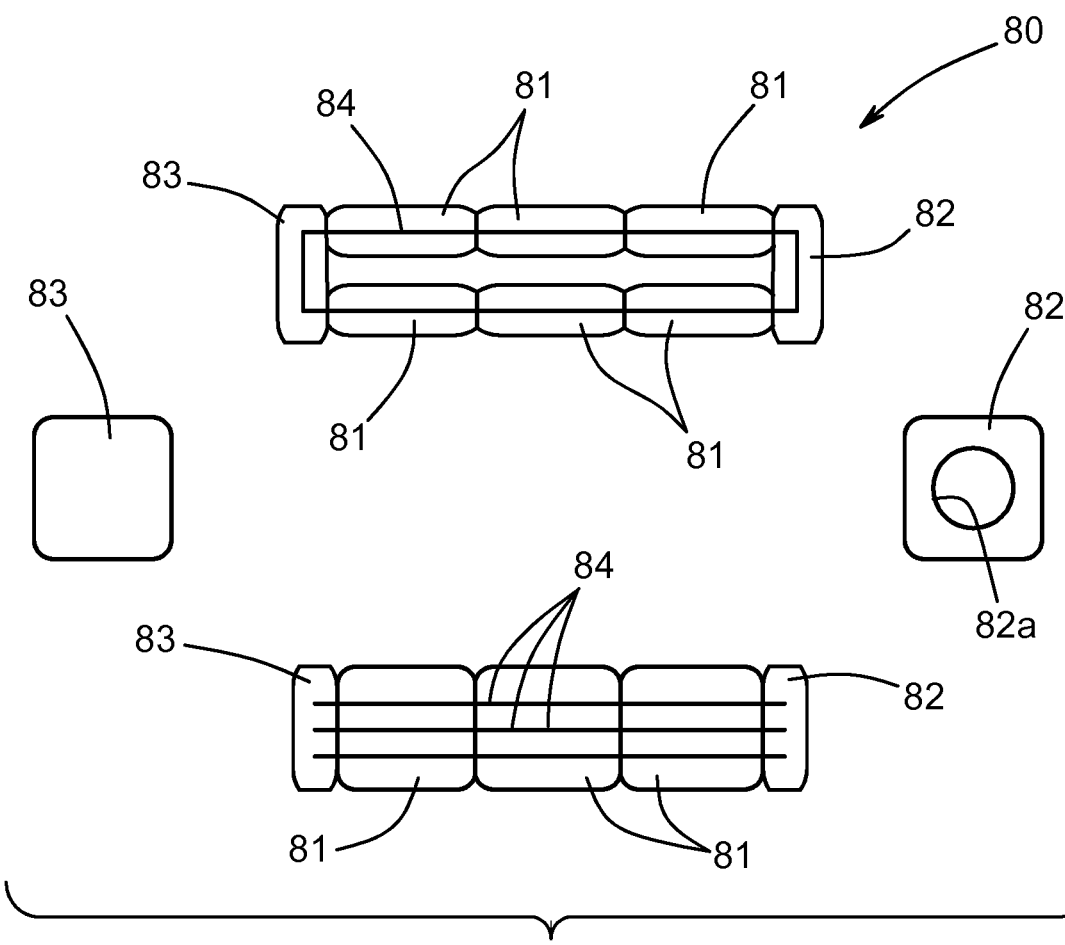
FIG. 35 is a series of views showing a seventh embodiment of an intervertebral cage in accordance with this invention.
Figure 36:
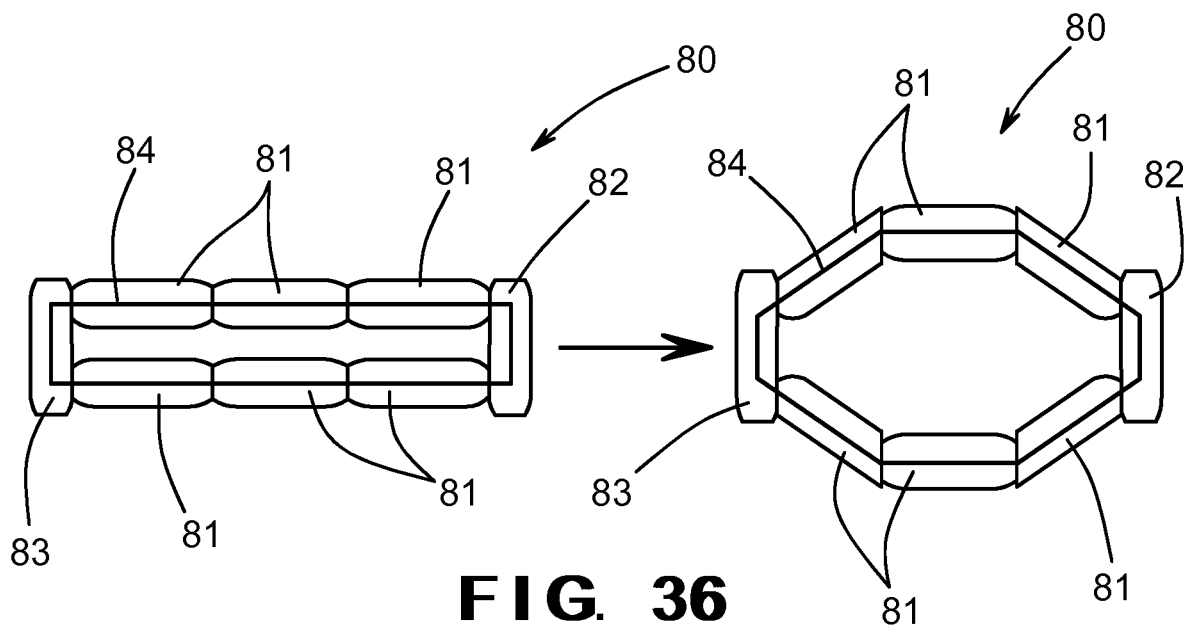
FIG. 36 is a pair of views showing the seventh embodiment of the intervertebral cage in both an initial contracted shape and a final implanted shape.

FIGS. 35 and 36 illustrate a seventh embodiment of an intervertebral cage, indicated generally at 80, in accordance with this invention. The seventh embodiment of the intervertebral cage 80 includes a plurality of side segments 81 and a plurality of end segments 82 and 83. In the illustrated embodiment, the intervertebral cage 80 includes six side segments 81 and two end segments 82 and 83, although a greater or lesser number of each may be provided. A wire or plurality of wires 84 extends in a closed loop through all of the segments 81, 82, and 83. In the illustrated embodiment, three of such wires 84 are utilized, although a greater or lesser number may be provided. The illustrated wires 84 extend generally parallel to one another, although such is not required. The end segment 82 is provided with a hole 82a that allows the insertion of a bone graft material therethrough. To accomplish this, the hole may have a threaded inner surface (not shown) that can cooperate with a complementary threaded outer surface provided on a cannulated device (not shown). The hole 82*a* can also be used for insertion of a balloon or other mechanical device to help in expansion of cage if required, as described below in connection with FIGS. 37 and 38. The wires 84 may be formed from a shape memory material, such as nitinol, that allows the intervertebral cage 80 to expand to the expanded shape, revert back to the initial contracted shape, or otherwise automatically acquire any other desired shape.

Figure 37:
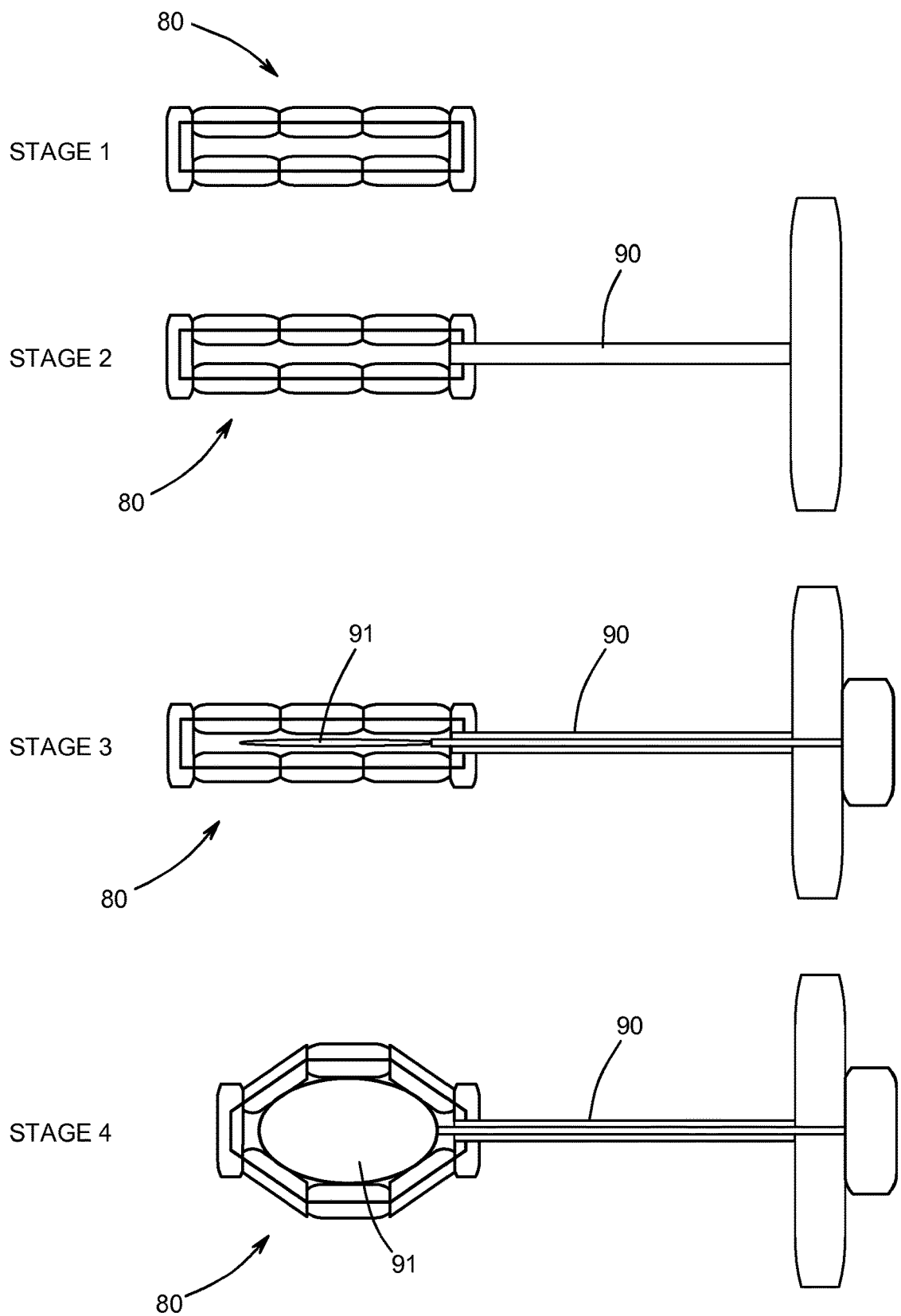
FIG. 37 is a series of views showing a first method for expanding the seventh embodiment of the intervertebral cage from the initial contracted shape to the final implanted shape.

FIG. 37 is a series of views showing a first method for expanding the seventh embodiment of the intervertebral cage 80 from the initial contracted shape to the final implanted shape. As shown therein, the hole 82*a* in the end segment 82 can be used for assisting in expansion of the intervertebral cage 80. Stage 1 shows the intervertebral cage 80 in its initial unexpanded condition. As shown in Stage 2, a cannulated instrument 90 having an outer threaded surface is initially attached to the inner threaded surface of the hole 82. Then, as shown in Stage 3, a deflated balloon 91 is inserted through the hole 82 into the interior of the intervertebral cage 80. Then, the balloon 91 is inflated as shown in Stage 4 to assist in the expansion of the intervertebral cage 80. It will be appreciated that this first method may be used to assist in the expansion of any of the embodiments of the intervertebral cage described above.

Figure 38:
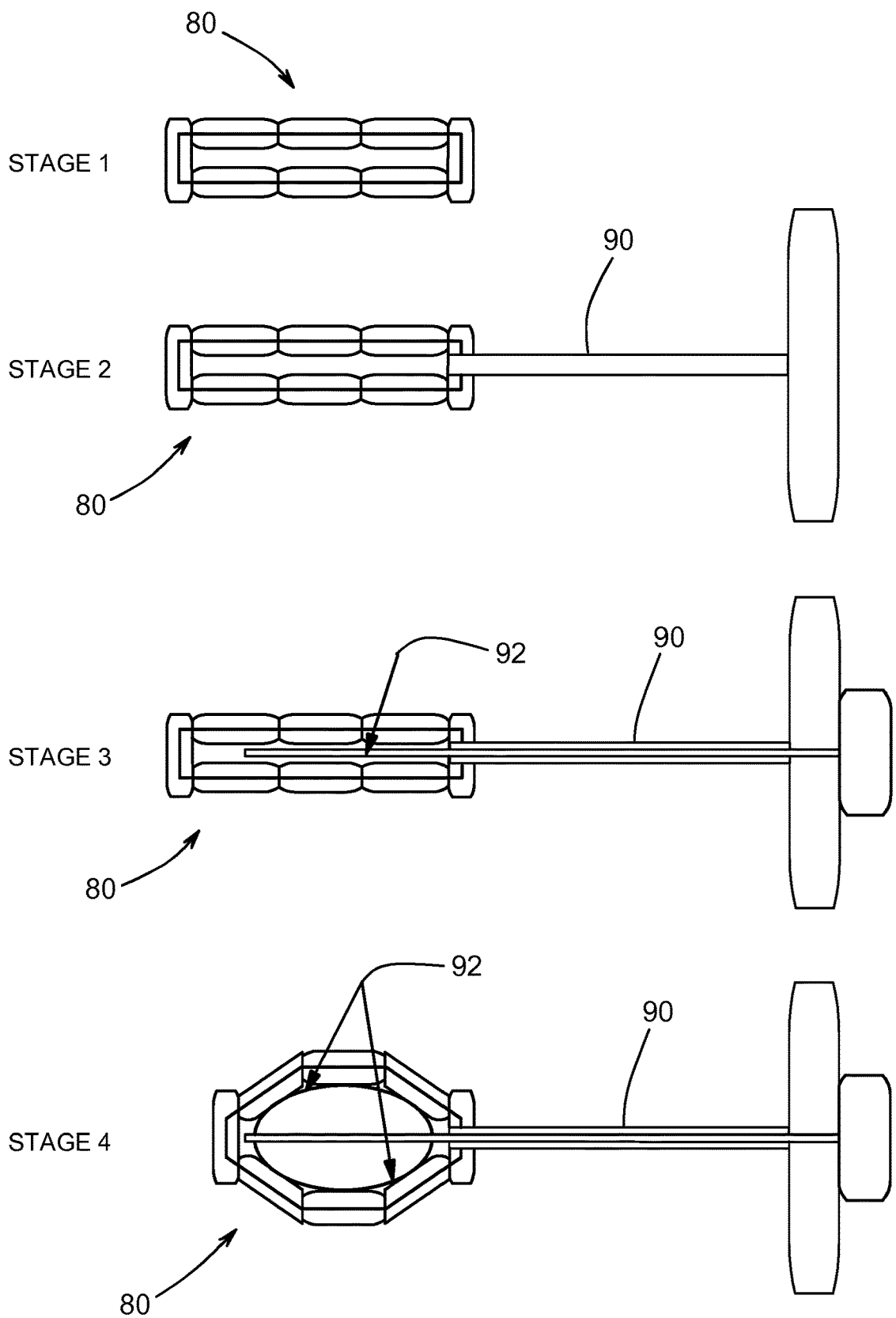
FIG. 38 is a series of views showing a second method for expanding the seventh embodiment of the intervertebral cage from the initial contracted shape to the final implanted shape.

FIG. 38 is a series of views showing a second method for expanding the seventh embodiment of the intervertebral cage 80 from the initial contracted shape to the final implanted shape. As shown therein, the hole 82*a* in the end segment 82 can be used for assisting in expansion of the intervertebral cage 80. Stage 1 shows the intervertebral cage 80 in its initial unexpanded condition. As shown in Stage 2, a cannulated instrument 90 having an outer threaded surface is initially attached to the inner threaded surface of the hole 82. Then, as shown in Stage 3, one or more (two in the illustrated embodiment) plates 92 are inserted through the hole 82 into the interior of the intervertebral cage 80. Then, the plates 92 are deformed as shown in Stage 4 to assist in the expansion of the intervertebral cage 80. The plates 92 may be two parallel nitinol plates that, by virtue of the inherent shape memory actuation, may be curved on opposite sides to expand the intervertebral cage 80 from the initial contracted shape to the final implanted shape. It will be appreciated that this second method may also be used to assist in the expansion of any of the embodiments of the intervertebral cage described above.

The principle and mode of operation of this invention have been explained and illustrated in its preferred embodiments. However, it must be understood that this invention may be practiced otherwise than as specifically explained and illustrated without departing from its spirit or scope.

What is claimed is:

1. An intervertebral cage comprising a plurality of preassembled segments that are connected together by one or more members formed from a shape memory alloy material, the one or more shape memory members holding the segments in place such that the segments form a closed ring, such that the segments are automatically moved from a generally linear initial orientation before implantation/insertion in an intervertebral space to a closed ring-shaped orientation after implantation/insertion in the intervertebral space;
wherein each of the plurality of segments has a passageway formed therethrough, wherein the passageway extends at both ends of each of the plurality of segments to define a first external recess and a second external recess of each of the plurality of segments;
wherein the first external recess is larger than the second external recess;
wherein an inner extent of the passageway of each of the plurality of segments is curved; and
wherein each of the plurality of segments includes a mating surface having interlocking protrusions provided thereon, wherein the interlocking protrusions provide a guide groove along a length of the intervertebral cage in the generally linear initial orientation.

2. The intervertebral cage defined in claim 1, wherein the one or more shape memory members form a wire or band that extends through each of the passageways.

3. The intervertebral cage defined in claim 1 wherein the passageway is a plurality of passageways, and wherein the one or more shape memory members form a wire that extends through one of the plurality of passageways of each of the plurality of segments.

4. The intervertebral cage defined in claim 1, wherein the one or more shape memory members form a wire that extends through each of the first and second external recesses.

5. The intervertebral cage defined in claim 1 wherein the shape memory alloy material demonstrates shape memory effects and superelasticity properties.

6. The intervertebral cage defined in claim 1 wherein the one or more members are formed from nitinol.

7. The intervertebral cage defined in claim 1 wherein the plurality of segments includes a plurality of side segments and first and second end segments, wherein the one or more members extend through the plurality of side segments and through the first and second end segments.

8. The intervertebral cage defined in claim 1 wherein the plurality of segments includes first and second pluralities of side segments and first and second end segments, and wherein the one or more members extend through the first and second pluralities of side segments and through the first and second end segments.

9. The intervertebral cage defined in claim 1, wherein the mating surfaces are generally cylindrical.

10. An intervertebral cage comprising a plurality of preassembled segments that are connected together by one or more members formed from a shape memory alloy material, the one or more shape memory members holding the segments in place such that the segments form a closed ring, and such that the segments are automatically moved from a generally linear initial orientation before implantation/insertion in an intervertebral space to a closed ring-shaped orientation after implantation/insertion in the intervertebral space;
wherein each of the plurality of segments includes a mating surface having interlocking protrusions provided thereon, wherein the mating surfaces are generally cylindrical to facilitate articulation of adjacent ones of the plurality of segments, and wherein the interlocking protrusions limit the amount of the articulation of the adjacent segments and provide a guide groove along a length of the intervertebral cage in the generally linear initial orientation;
wherein each of the plurality of segments has a passageway formed therethrough; and
wherein an inner extent of the passageway of each of the plurality of segments is curved.

* * * * *